United States Patent

Inui et al.

[11] Patent Number: 5,914,361
[45] Date of Patent: Jun. 22, 1999

[54] CYCLIC PHOSPHONITES AND THEIR USE AS STABILIZERS FOR ORGANIC MATERIALS

[75] Inventors: Naoki Inui, Nara; Taketoshi Kikuchi; Kanako Fukuda, both of Osaka, all of Japan

[73] Assignee: Sumitomo Chemical Company, Limited, Osaka, Japan

[21] Appl. No.: 08/917,553

[22] Filed: Aug. 26, 1997

[30] Foreign Application Priority Data

Aug. 26, 1996 [JP] Japan ................................. 8-223779

[51] Int. Cl.$^6$ ...................... C08K 5/5377; C07F 9/6574
[52] U.S. Cl. ............... 524/117; 252/400.21; 252/400.24; 524/119; 558/76; 558/82
[58] Field of Search ............................... 558/82; 524/117

[56] References Cited

U.S. PATENT DOCUMENTS

| | | | |
|---|---|---|---|
| 4,276,232 | 6/1981 | Rasberger | 558/82 |
| 5,698,729 | 12/1997 | Kleiner | 558/82 |

FOREIGN PATENT DOCUMENTS

| | | |
|---|---|---|
| 05086084 | 5/1993 | Japan . |
| 05222250 | 8/1993 | Japan . |
| 05222256 | 8/1993 | Japan . |
| 05331313 | 12/1993 | Japan . |

OTHER PUBLICATIONS

Database CAPLUS on STN®, Chemical Abstracts Service, (Columbus, Ohio), Accession No. 1984:492945; Japan Kokai Tokkyo Koho 59–043038, Mar. 1984, abstract, 1984.
Database CAPLUS on STN®, Chemical Abstracts Services, (Columbus, Ohio), Accession No. 1983:17530; Japan Kokai Tokkyo Koho 57–105451, Jun. 1982, abstract, 1983.

*Primary Examiner*—Michael G. Ambrose
*Attorney, Agent, or Firm*—Pillsbury Madison & Sutro LLP

[57] ABSTRACT

Phosphonites which are useful as a deterioration inhibitor for organic material and are represented by the following formula:

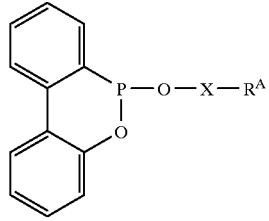

(I)

wherein X represents a connecting group, and $R^A$ represents a phenyl group which may be optionally substituted; and a process for producing the same are provided.

10 Claims, No Drawings

CYCLIC PHOSPHONITES AND THEIR USE AS STABILIZERS FOR ORGANIC MATERIALS

FIELD OF THE INVENTION

The present invention relates to novel phosphonites, process for producing them and their use as a stabilizer for organic materials.

BACKGROUND OF THE INVENTION

It has been known that organic materials such as thermoplastic resin, thermosetting resin, natural or synthetic rubber, mineral oil, lubricating oil, adhesive, paint, etc. are deteriorated by an action such as heat, oxygen, etc. on production, processing and use to cause deterioration of the strength of the organic material due to a phenomenon (e.g. molecular cleavage, molecular closslinking, etc.), change in flow properties, coloring, deterioration of surface physical properties, etc., which results in decrease of a commercial value. It has hitherto been known that the organic material is stabilized by containing various phenol and phosphorous antioxidants for the purpose of solving these problems about heat deterioration and oxidization deterioration.

As the phosphorous antioxidant, for example, tris(2,4-di-t-butylphenyl)phosphite is used.

However, these known phosphorous antioxidants had a problem that the stabilizing effect to heat deterioration and oxidization deterioration is insufficient.

On the other hand, eight-membered ring phosphites such as 2,10-dimethyl-4,8-di-t-butyl-6-{2-[3-(3-t-butyl-4-hydroxy-5-methylphenyl)propionyloxy]ethyl-12H-dibenzo[d,g][1,3,2]dioxaphosphosin and the like, on which a phenyl group is substituted through a connecting group, an alkylcarbonyloxyalkyl group, have been proposed as means for solving these problems of the phosphorous antioxidant (JP-A-5-86084). However, the stabilizing effect of these eight-membered ring phosphates is not necessarily sufficient, although it has improved.

Six-membered ring phosphites such as 2,4-di-t-butyl-6-[3,5-di-t-butyl-6-((6H-dibenzo[c,e][1,2]oxaphosphorine-6-yl)oxy)benzyl]phenol, on which a phenyl group is substituted directly, have also been proposed (JP-A-5-222250, JP-A-5-222256, JP-A-5-331313). However, there is a problem that it is liable to color the organic materials.

The present inventors have produced various phosphorous compounds and studied intensively about them. As a result, it has been found that specific six-membered ring phosphonites, on which a phenyl group is substituted through a connecting group, exhibit not only stabilizing effects same to or superior to those of the eight-membered ring phosphites mentioned but also superior anti-cloration effect to that of the above-mentioned six-membered ring phosphites, on which a phenyl group is substituted directly. Thus, the present invention has been accomplished.

SUMMARY OF THE INVENTION

The present invention provides phosphonites represented by the formula (I):

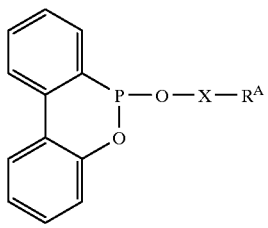

(I)

wherein X represents a connecting group, and $R^A$ represents a phenyl group which may be optionally substituted.

The present invention also provides a process for producing the phosphonites represented by the formula (I) and their use.

DETAILED DESCRIPTION OF THE INVENTION

Examples of the connecting group X in the formula (I) include a divalent connecting group which may have a hetero atom and the total carbon number of which is about 1–20. Specific examples of the connecting group X include a group represented by the following formula (II), (III), (IV), (V), (VI), (VII) or (VIII):

 (II)

 (III)

 (IV)

 (V)

 (VI)

 (VII)

 (VIII)

herein * indicates the bond connecting to the oxygen atom, D represents an alkylene group having 1–8 carbon atoms, A represents a direct bond or an alkylene group having 1–8 carbon atoms, B represents a dihydric alcohol residue, G represents an alkylene group having 2–8 carbon atoms, and $R^1$ represents a hydrogen atom, an alkyl group having 1–8 carbon atoms or a group represented by the following formula (IX):

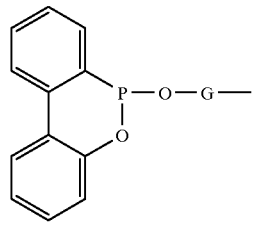

(IX)

wherein G is as defined above.

Examples of the alkylene group having 1–8 carbon atoms, as D or A, include linear alkylene such as methylene, ethylene, propylene, butylene, pentamethylene, hexamethylene and octamethylene, and branched alkylene such as 1-methylethylene, dimethylethylene and 2,2-dimethyl-1,3-propylene.

The dihydric alcohol residue represented by B means a group corresponding to a dihydric alcohol excluding two hydroxy groups. Typical examples the dihydric alcohol residue include residues of alkylenediols, such as ethylene glycol, 1,2-propanediol, 1,3-propanediol, 1,2-butanediol, 1,3-butanediol, 1,4-butanediol, 2,3-butanediol, 2-methyl-1, 3-propanediol, 1,2-pentanediol, 1,5-pentanediol, 2,4-pentanediol, neopentyl glycol, 1,2-hexanediol, 1,5-hexanediol, 1,6-hexanediol, 2,5-hexanediol, 2-methyl-2,4-pentanediol, 2-methyl-1,5-pentanediol, 3,3-dimethylbutanediol, 2,3-dimethyl-2,3-butanediol, 2-ethyl-2-methyl-1,3-propanediol, 2,2-diethyl-1,3-propanediol, 2,4-dimethyl-2,4-pentanediol, 1,2-octanediol, 1,8-octanediol, 2,5-dimethyl-2,5-hexanediol, 2-ethyl-1,3-hexanediol, 2,2,4-trimethyl-1,3-pentanediol, 1,9-nonanediol, 2-butyl-2-ethyl-1,3-propanediol, 1,2-decanediol, 1,10-decanediol, 1,12-dodecanediol, 1,2-tetradecanediol, 1,14-tetradecanediol, 1,2-hexadecanediol and 1,16-hexadecanediol; residues of diols having a double bond, preferably containing 4 to 8 carbon atoms, such as 2-butene-1,4-diol, 2-methylene-1,3-propanediol, 5-hexene-1,2-diol and 7-octene-1,2-diol; residues of cyclic diols, such as 1,2-cyclopentanediol, 1,3-cyclopentanediol, 1,2-cyclohexanediol, 1,3-cyclohexanediol, 1,4-cyclohexanediol, 1,2-cyclooctanediol, 1,4-cyclooctanediol, 1,5-cyclooctanediol, p-menthane-3,8-diol and 4,4'-isopropylidenedicyclohexanol; and residues of diols having one or more hetero atoms in addition to the oxygen atoms of the alcohol moieties, such as diethylene glycol, triethylene glycol 3,9-bis(1,1-dimethyl-2-hydroxyethyl)-2,4,8,10-tetraoxaspiro[5,5]undecane, neopentyl glycol hydroxypivalate, 2,2'-thiodiethanol, 2-methylthio-1,2-propanediol and diethanolamine.

Examples of the alkylene group having 2 to 8 carbon atoms, represented by G, include linear alkylene such as ethylene, propylene, butylene, pentamethylene, hexamethylene and octamethylene, and branched alkylene such as 1-methylethylene, 2,2-dimethyl-1 and 3-propylene.

Examples of alkyl groups having 1 to 8 carbon atoms, represented by $R^1$, include methyl, ethyl, n-propyl, i-propyl, n-butyl, i-butyl, sec-butyl, t-butyl, t-pentyl, i-octyl, t-octyl and 2-ethylhexyl.

D is preferably ethylene, propylene, 2,2-dimethyl- 1,3-propylene, etc. when the connecting group X is a group of formula (II).

A is preferably methylene and B is preferably ethylene, propylene, etc. when the connecting group X is a group of formula (III).

A is preferably a direct bond, ethylene, etc. when the connecting group X is a group of the formula (IV); or A is preferably a direct bond, ethylene, dimethylmethylene, etc. and B is preferably ethylene glycol residue, 1,2-propanediol residue, etc, when the connecting group X is a group of the formula (V).

A is preferably a direct bond, methylene, etc. and D is preferably methylene, etc. when the connecting group X is a group of the formula (VI).

A is preferably methylene, ethylene, etc. and G is preferably ethylene, propylene, etc. and $R^1$ is preferably hydrogen, methyl, ethyl, a formula (IX), etc. when the connecting group X is a group of the formula (VII).

A is preferably a direct bond, ethylene, etc., G is preferably ethylene, propylene, etc. and $R^1$ is preferably hydrogen, methyl, ethyl, a formula (IX), etc. when the connecting group X is a group of formula (VIII).

$R^A$ in the present invention represents an optionally substituted phenyl group, and examples the substituent include alkyl group having 1 to 8 carbon atoms, cycloalkyl group having 5 to 8 carbon atoms, alkylcycloalkyl group having 6 to 12 carbon atoms, aralkyl group having 7 to 12 carbon atoms, phenyl group, hydroxyl group, alkoxy group having 7 to 12 carbon atoms, aralkyloxy group having 7 to 12 carbon atoms, etc.

Examples of the phenyl group include groups of the formula (X):

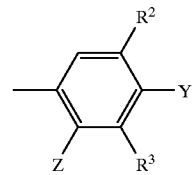

wherein $R^2$ and $R^3$ independently represent hydrogen, an alkyl group having 1 to 8 carbon atoms, a cycloalkyl group having 5 to 8 carbon atoms, an alkylcycloalkyl group having 6 to 12 carbon atoms, an aralkyl or phenyl group having 7 to 12 carbon atoms; and Y and Z independently represent hydrogen, an alkyl group having 1 to 8 carbon atoms, a cycloalkyl group having 5 to 8 carbon atoms, an alkylcycloalkyl group having 6 to 12 carbon atoms, an aralkyl group having 7 to 12 carbon atoms, a phenyl group, a hydroxyl group, an alkoxy group having 1 to 8 carbon atoms or an aralkyloxy group having 7 to 12 carbon atoms.

Examples of the alkyl group having 1 to 8 carbon atoms include methyl, ethyl, n-propyl, i-propyl, n-butyl, i-butyl, sec-butyl, t-butyl, t-pentyl, i-octyl, t-octyl and 2-ethylhexyl.

Examples of the cycloalkyl group having 5 to 8 carbon atoms include cyclopentyl, cyclohexyl, cycloheptyl, cyclooctyl, etc., and examples of the alkylcycloalkyl group having 6 to 12 carbon atoms include 1-methylcyclopentyl, 1-methylcyclohexyl, 1-methyl-4-i-propylcyclohexyl, etc.

Examples of the aralkyl group having 7 to 12 carbon atoms include benzyl, α-methylbenzyl, α, α-dimethylbenzyl, etc.

Examples of the alkoxyl group having 1 to 8 carbon atoms include alkoxyl groups whose alkyl moiety is methyl, ethyl, n-propyl, i-propyl, n-butyl, i-butyl, sec-butyl, t-butyl, t-pentyl, i-octyl, t-octyl or 2-ethylhexyl, and examples of the aralkyloxy group having 7 to 12 carbon include aralkyloxy groups whose aralkyl moiety is benzyl, α-methylbenzyl or α, α-dimethylbenzyl.

$R^2$, $R^3$ are preferably hydrogen, methyl, t-butyl, t-pentyl, t-octyl, 1-methylcyclohexyl, etc.

It is preferred that one of Y and Z is a hydroxyl group, an alkoxyl group having 1 to 8 carbon atoms or an aralkyloxy group having 7 to 12 carbon atoms while the other is hydrogen or an alkyl group having 1 to 8 carbon atoms. More preferably, one of them is a hydroxyl group or a methoxy group.

Phosphorous esters of the above formula (I) can be produced, for example, by reacting halogenophosphorine of the formula (XI)

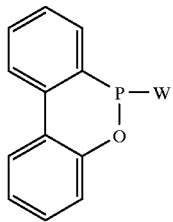

(XI)

wherein W represents halogen with a hydroxy compound of the formula (XII):

HO—X—R$^A$ (XII)

wherein X and R$^A$ are same as defined above.

The reaction can also be accelerated in the copresence of dehydrohalogenating agent such as amines, pyridines, pyrrolidines, amides, etc., and hydroxides of alkali metals or alkaline earth metals.

The amines may be primary amine, secondary amine or tertiary amine, and examples thereof include t-butylamine, t-pentylamine, t-hexylamine, t-octylamine, di-t-butylamine, di-t-pentylamine, di-t-hexylamine, di-t-octylamine, trimethylamine, triethylamine, N,N-dimethylaniline, N,N-diethylaniline, preferably triethylamine.

Pyridines include pyridine, picoline, preferably pyridine. Pyrrolidines include, for example, 1-methyl-2-pyrrolidine.

As the amides, for example, N,N-dimethylformamide, N,N-dimethylacetamide, and N,N-dimethylformamide are preferably used.

Examples of the hydroxides of alkali metals or alkali earth metals include sodium hydroxide, potassium hydroxide, etc., preferably sodium hydroxide.

The reaction is normally carried out in an organic solvent. The organic solvent is not specifically limited unless the reaction is not inhibited, and examples thereof include aromatic hydrocarbon, aliphatic hydrocarbon, oxygen-containing hydrocarbon, halogenated hydrocarbon, etc.

Examples of the aromatic hydrocarbon include benzene, toluene, xylene, ethylbenzene, etc.; examples of the aliphatic hydrocarbon include n-hexane, n-heptane, n-octane, etc.; examples of the oxygen-containing hydrocarbon include diethylether, dibutylether, tetrahydrofuran, 1,4-dioxane, etc.; and examples of the halogenated hydrocarbon include chloroform, carbon tetrachloride, monochlorobenzene, dichloromethane, 1,2-dichloroethane, dichlorobenzene, etc.

Among them, toluene, xylene, n-hexane, n-heptane, diethylether, tetrahydrofuran, 1,4-dioxane, chloroform, dichloromethane etc. are preferably used.

As the reaction method, a method of reacting a halogenophosphorine of the formula (XI) with a hydroxyl compound of the formula (XII) in the presence of a dehydrohalogenating agent is normally adopted.

In case of this method, the hydroxyl compound (XII) is preferably used in an amount of about 0.9 to 1.1 mols, more preferably 0.95 to 1.05 mols per mol of the halogenophosphorine (XI).

When the dehydrohalogenating agent is used, it is preferably used in an amount of 1 to 2 mols, more preferably 1 to 1.3 mols, per mol of the halogenophosphorine (XI).

The reaction temperature is normally within the range from 0 to 200° C.

After the completion of the reaction, when using a dehydrohalogenating agent, the phosphite (I) of the present invention can be obtained by removing hydrogenhaloganate of the dehydrohalogenating agent produced by the reaction, removing the solvent and subjecting the resultant to an appropriate post-treatment such as a crystallization, column chromatography, etc.

Examples of W in the halogenophosphorine (XI) as a raw material for phosphite (I) include halogen such as fluorine, chlorine, bromine, etc.

The halogenophosphorine (XI) can be produced by reacting 2-phenylphenol to with phosphorous trihalide such as phosphorus trichloride using a Friedel-Crafts catalyst such as zinc chloride, aluminum chloride, etc., according to the method described in Phosphorus and Sulfur 31.,71 (1987).

Examples for the hydroxide compound (XII) as the other raw material include, when the connecting group X is represented by the formula (II), 2-(3-t-butyl-4-hydroxyphenyl)ethanol, 2-(3-t-pentyl-4-hydroxyphenyl)ethanol, 2-(3-t-octyl-4-hydroxyphenyl)ethanol, 2-(3-cyclohexyl-4-hydroxyphenyl)ethanol, 2-[3-(1-methylcyclohexyl)-4-hydroxyphenyl]ethanol, 2-(3-t-butyl-4-hydroxy-5-methylphenyl)ethanol, 2-(3-t-pentyl-4-hydroxy-5-methylphenyl)ethanol, 2-(3-t-octyl-4-hydroxy-5-methylphenyl)ethanol, 2-(3-cyclohexyl-4-hydroxy-5-methylphenyl)ethanol, 2-[3-(1-methylcyclohexyl)-4-hydroxy-5-methylphenyl]ethanol, 2-(3-t-butyl-4-hydroxy-5-ethylphenyl)ethanol, 2-(3-t-pentyl-4-hydroxy-5-ethylphenyl)ethanol, 2-(3-t-octyl-4-hydroxy-5-ethylphenyl)ethanol, 2-(3-cyclohexyl-4-hydroxy-5-ethylphenyl)ethanol, 2-[3-(1-methylcyclohexyl)-4-hydroxy-5-ethylphenyl]ethanol, 2-(3,5-di-t-butyl-4-hydroxyphenyl)ethanol, 2-(3-t-pentyl-4-hydroxy-5-t-butylphenyl)ethanol, 2-(3-t-octyl-4-hydroxy-5-t-butylphenyl)ethanol, 2-(3-t-cyclohexyl-4-hydroxy-5-t-butylphenyl)ethanol, 2-[3-(1-methylcyclohexyl)-4-hydroxy-5-t-butylphenyl]ethanol, 2-(3-t-butyl-4-methoxyphenyl)ethanol, 2-(3-t-pentyl-4-methoxyphenyl)ethanol, 2-(3-t-octyl-4-methoxyphenyl)ethanol, 2-(3-cyclohexyl-4-methoxyphenyl)ethanol, 2-[3-(1-methylcyclohexyl)-4-methoxyphenyl]ethanol, 2-(3-t-butyl-4-methoxy-5-methylphenyl)ethanol, 2-(3-t-pentyl-4-methoxy-5-methylphenyl)ethanol, 2-(3-t-octyl-4-methoxy-5-methylphenyl)ethanol, 2-(3-cyclohexyl-4-methoxy-5-methylphenyl)ethanol, 2-[3-(1-methylcyclohexyl)-4-methoxy-5-methylphenyl]ethanol, 2-(3-t-butyl-4-methoxy-5-ethylphenyl)ethanol, 2-(3-t-pentyl-4-methoxy-5-ethylphenyl)ethanol, 2-(3-t-octyl-4-methoxy-5-ethylphenyl)ethanol, 2-(3-cyclohexyl-4-methoxy-5-ethylphenyl)ethanol, 2-[3-(1-methylcyclohexyl)-4-methoxy-5-ethylphenyl]ethanol, 2-(3,5-di-t-butyl-4-methoxyphenyl)ethanol, 2-(3-t-pentyl-4-methoxy-5-t-butylphenyl)ethanol, 2-(3-t-octyl-4-methoxy-5-t-butylphenyl)ethanol, 2-(3-cyclohexyl-4-methoxy-5-t-butylphenyl)ethanol, 2-[3-(1-methylcyclohexyl)-4-methoxy-5-t-butylphenyl]ethanol, 3-(3-t-butyl-2-hydroxyphenyl)propanol, 3-(3-t-butyl-4-hydroxyphenyl)propanol, 3-(5-t-butyl-2-hydroxyphenyl)propanol, 3-(3-t-pentyl-4-hydroxyphenyl)propanol, 3-(3-t-octyl-4-hydroxyphenyl)propanol, 3-(3-cyclohexyl-4-hydroxyphenyl)propanol, 3-[3-(1-methylcyclohexyl)-4-hydroxyphenyl]propanol, 3-(3-t-butyl-2-hydroxy-5-methylphenyl)propanol, 3-(3-t-butyl-4-hydroxy-5-methylphenyl)propanol, 3-(5-t-butyl-2-hydroxy-3-methylphenyl)propanol, 3-(3-t-pentyl-4-hydroxy-5-methylphenyl)propanol, 3-(3-t-octyl-4-hydroxy-5-methylphenyl)propanol, 3-(3-cyclohexyl-4-hydroxy-5-methylphenyl)propanol, 3-[3-(1-methylcyclohexyl)-4-hydroxy-5-methylphenyl]propanol, 3-(3-t-butyl-4-hydroxy-5-ethylphenyl)propanol, 3-(3-t-pentyl-4-hydroxy-5-ethylphenyl)propanol, 3-(3-t-octyl-4-hydroxy-5- ethylphenyl)propanol, 3-(3-cyclohexyl-4-hydroxy-5-ethylphenyl)propanol, 3-[3-(1-methylcyclohexyl)-4-hydroxy-5-ethylphenyl]propanol, 3-(3,5-di-t-butyl-2-hydroxyphenyl)propanol, 3-(3,5-di-t-butyl-4-hydroxyphenyl)propanol, 3-(3-t-pentyl-4-hydroxy-5-t-butylphenyl)propanol, 3-(3-t-octyl-4-hydroxy-5-t-butylphenyl)propanol, 3-(3-cyclohexyl-4-hydroxy-5-t-buthylphenyl)propanol, 3-[3-(1-methylcyclohexyl)-4-hydroxy-5-t-buthylphenyl]propanol, 3-(3-t-butyl-2-methoxyphenyl)propanol, 3-(3-t-butyl-4-methoxyphenyl) propanol, 3-(3-t-butyl-5-methoxyphenyl)propanol, 3-(3-t-penzyl-4-methoxyphenyl)propanol, 3-(3-t-octyl-4-methoxyphenyl)propanol, 3-(3-cyclohexyl-4-methoxyphenyl)propanol, 3-[3-(1-methylcyclohexyl)-4-methoxyphenyl]propanol, 3-(3-t-butyl-2-methoxy-5-methylphenyl)propanol, 3-(3-t-butyl-4-methoxy-5-methylphenyl)propanol, 3-(5-t-butyl-2-methoxy-3-methylphenyl)propanol, 3-(3-t-pentyl-4-methoxy-5-methylphenyl)propanol, 3-(3-t-octyl-4-methoxy-5-methylphenyl)propanol, 3-(3-cyclohexyl-4-methoxy-5-methylphenyl)propanol, 3-[3-(1-methylcyclohexyl)-4-methoxy-5-methylphenyl]propanol, 3-(3-t-butyl-4-methoxy-5-ethylphenyl)propanol, 3-(3-t-pentyl-4-methoxy-5-ethylphenyl)propanol, 3-(3-t-octyl-4-methoxy-5-ethylphenyl)propanol, 3-(3-cyclohexyl-4-methoxy-5-ethylphenyl)propanol, 3-[3-(1-methylcyclohexyl)-4-methoxy-5-ethylphenyl]propanol, 3-(3,5-di-t-butyl-2-methoxyphenyl)propanol, 3-(3,5-di-t-butyl-4-methoxyphenyl)propanol, 3-(3-t-pentyl-4-methoxy-5-t-butylphenyl)propanol, 3-(3-t-octyl-4-methoxy-5-t-butylphenyl)propanol, 3-(3-cyclohexyl-4-methoxy-5-t-buthylphenyl)propanol, 3-[3-(1-methylcyclohexyl)-4-methoxy- 5-t-buthylphenyl]propanol, 3-(3-t-butyl-2-ethoxyphenyl)propanol, 3-(3-t-butyl-4-ethoxyphenyl) propanol, 3-(3-t-butyl-4-ethoxy-5-methylphenyl)propanol, 3-(3-t-butyl-2-ethoxy-5-methylphenyl)propanol, 3-(5-t-butyl-2-ethoxy-3-methylphenyl)propanol, 3-(3,5-di-t-butyl-4-ethoxyphenyl)propanol, 3-(3,-5-di-t-butyl-2-ethoxyphenyl)propanol, 4-(3-t-butyl-2-hydroxyphenyl)butanol, 4-(3-t-butyl-4-hydroxyphenyl)butanol, 4-(3-t-butyl-4-hydroxy-5-methylphenyl)butanol, 4-(3-t-butyl-2-hydroxy-5-methylphenyl)butanol, 4-(5-t-butyl-2-hydroxy-3-methylphenyl)butanol, 4-(3,5-di-t-butyl-4-hydroxyphenyl)butanol, 4-(3,5-di-t-butyl-2-hydroxyphenyl)butanol, 4-(3-t-butyl-2-methoxyphenyl)butanol, 4-(3-t-butyl-4-nethoxyphenyl)butanol, 4-(3-t-butyl-4-methoxy-5-methylphenyl)butanol, 4-(3-t-butyl-2-methoxy-5-methylphenyl)butanol, 4-(5-t-butyl-2-methoxy-3-methylphenyl)butanol, 4-(3,5-di-t-butyl-4-methoxyphenyl)butanol, 4-(3,5-di-t-butyl-2-methoxyphenyl)butanol, 5-(3-t-butyl-2-hydroxyphenyl)pentanol, 5-(3-t-butyl-4-hydroxyphenyl)pentanol, 5-(3-t-butyl-4-hydroxy-5-methylphenyl)pentanol, 5-(3-t-butyl-2-hydroxy-5-methylphenyl)pentanol, 5-(5-t-butyl-2-hydroxy-3-methylphenyl)pentanol, 5-(3,5-di-t-butyl-4-hydroxyphenyl) pentanol, 6-(3,5-di-t-butyl- 2-hydroxyphenyl)hexanol, 6-(3-t-butyl-2-hydroxyphenyl)hexanol, 6-(3-t-butyl-4-hydroxyphenyl)hexanol, 6-(3-t-butyl-4-hydroxy-5-methylphenyl)hexanol, 6-(3-t-butyl-2-hydroxy-5-methylphenyl)hexanol, 6-(5-t-butyl-2-hydroxy-3-methylphenyl)hexanol, 6-(3,5-di-t-butyl-4-hydroxyphenyl) hexanol and 6-(3,5-di-t-butyl-2-hydroxyphenyl)hexanol.

These compounds can be produced by reducing the corresponding phenylcarboxylic acids, or esters thereof, or benzaldehydes according to the known method.

When the connecting group X is a group of the formula (III), examples of the hydroxyl compound (XII) include 2-(3-t-butyl-2-hydroxyphenylmethyloxy)ethanol, 2-(3-t-butyl-4-hydroxyphenylmethyloxy)ethanol, 2-(3-t-butyl-2-hydroxy-5-methylphenylmethyloxy)ethanol, 2-(3,5-di-t-butyl-2-hydroxyphenylmethyloxy)ethanol, 2-(3-t-butyl-4-hydroxy-5-methylphenylmethyloxy)ethanol, 2-(3,5-di-t-butyl-4-hydroxyphenylmethyloxy)ethanol, 2-(2-methyl-3,5-di-t-butyl-4-hydroxyphenylmethyloxy)ethanol, 2-(3-t-butyl-2-methoxyphenylmethyloxy)ethanol, 2-(3-t-butyl-4-methoxyphenylmethyloxy)ethanol, 2-(3-t-butyl-2-methoxy-5-methylphenylmethyloxy)ethanol, 2-(3,5-di-t-butyl-2-methoxyphenylmethyloxy)ethanol, 2-(3-t-butyl-4-methoxy-5-methylphenylmethyloxy)ethanol, 2-(3,5-di-t-butyl-4-methoxyphenylmethyloxy)ethanol, 2-(2-methyl-3,5-di-t-butyl-4-methoxyphenylmethyloxy)ethanol, 3-(3-t-butyl-2-hydroxyphenylmethyloxy)propanol, 3-( 3-t-butyl-4-hydroxyphenylmethyloxy)propanol, 3-(3-t-butyl-2-hydroxy-5-methylphenylmethyloxy)propanol, 3-(3,5-di-t-butyl-2-hydroxyphenylmethyloxy)propanol, 3-(3-t-butyl-4-hydroxy-5-methylphenylmethyloxy)propanol, 3-(3,5-di-t-butyl-4-hydroxyphenylmethyloxy)propanol, 3-(2-methyl-3,5-di-t-butyl-4-hydroxyphenylmethyloxy)propanol, 3-(3-t-butyl-2-methoxyphenylmethyloxy)propanol, 2-(3-t-butyl-4-methoxyphenylmethyloxy)propanol1, 2-(3-t-butyl-2-methoxy-5-methylphenylmethyloxy)propanol, 2-(3,5-di-t-butyl-2-methoxyphenylmethyloxy)propanol, 2-(3-t-butyl-4-methoxy-5-methylphenylmethyloxy)propanol, 3-(3,5-di-t-butyl-4-methoxyphenylmethyloxy)propanol, 3-(2-methyl-3,5-di-t-butyl-4-methoxyphenylmethyloxy)propanol, 4-(3-t-butyl-2-hydroxyphenylmethyloxy)butanol, 4-(3-t-butyl-4-hydroxyphenylmethyloxy)butanol, 4-(3-t-butyl-2-hydroxy-5-methylphenylmethyloxy)butanol, 4-(3,5-di-t-butyl-2-hydroxyphenylmethyloxy)butanol, 4-(3-t-butyl-4-hydroxy-5-methylphenylmethyloxy)butanol, 4-(3,5-di-t-butyl-4-hydroxyphenylmethyloxy)butanol, 4-(2-methyl-3,5-di-t-butyl-4-hydroxyphenylmethyloxy)butanol, 4-(3-t-butyl-2-methoxyphenylmethyloxy)butanol, 2-(3-t-butyl-4-methoxyphenylmethyloxy)butanol, 2-(3-t-butyl-2-methoxy-5-methylphenylmethyloxy)butanol, 2-(3,5-di-t-butyl-2-methoxyphenylmethyloxy)butanol, 2-(3-t-butyl-4-methoxy-5-methylphenylmethyloxy)butanol, 4-(3,5-di-t-butyl-4-methoxyphenylmethyloxy)butanol and 4-(2-methyl-3,5-di-t-butyl- 4-methoxyphenylmethyloxy)butanol.

When A is methylene, these compounds can be produced, for example, by reacting the corresponding diol with the corresponding phenol compound and formaldehyde. When A is an alkylene other than methylene, the compounds can be produced, for example, by reacting the corresponding diol with the corresponding halide.

When the connecting group X is a group of the formula (IV), examples of the hydroxy compound (XII) include carboxylic acids such as 3-t-butyl-2-hydroxybenzoic acid, 3-t-butyl-4-hydroxybenzoic acid, 5-t-butyl-2-hydroxybenzoic acid, 3-t-pentyl-4-hydroxybenzoic acid, 3-t-octyl-4-hydroxybenzoic acid, 3-cyclohexyl-4-hydroxybenzoic acid, 3-(1-methylcyclohexyl)-4-hydroxybenzoic acid, 3-t-butyl-2-hydroxy-5-methylbenzoic acid, 3-t-butyl-4-hydroxy-5-methylbenzoic acid, 5-t-butyl-2-hydroxy-3-methylbenzoic acid, 3-t-pentyl-4-hydroxy-5-methylbenzoic acid, 3-t-octyl-4-hydroxy-5-methylbenzoic acid, 3-cyclohexyl-4-hydroxy-5-methylbenzoic acid, 3-(1-methylcyclohexyl)-4-hydroxy-5-methylbenzoic acid, 3-t-butyl-4-hydroxy-5-ethylbenzoic acid, 3-t-pentyl-4-hydroxy-5-ethylbenzoic acid, 3-t-octyl-4-hydroxy-5-ethylbenzoic acid, 3-cyclohexyl-4-hydroxy-5-ethylbenzoic acid, 3-(1-methylcyclohexyl)-4-hydroxy-5-ethylbenzoic acid, 3,5-di-t-butyl-2-hydroxybenzoic acid, 3,5-di-t-butyl-4-hydroxybenzoic acid, 3-t-pentyl-4-hydroxy-5-t- butylbenzoic acid, 3-t-octyl- 4-hydroxy-5-t-butylbenzoic acid, 3-cyclohexyl-4-hydroxy-5-t-butylbenzoic acid, 3-(1-methylcyclohexyl)-4-hydroxy-5-t-butylbenzoic acid, 3-t-butyl-2-methoxybenzoic acid, 3-t-butyl-4-methoxybenzoic acid, 3-t-butyl-5-methoxybenzoic acid, 3-t-pentyl-4-methoxybenzoic acid, 3-t-octyl-4-methoxybenzoic acid, 3-cyclohexyl-4-methoxybenzoic acid, 3-(1-methylcyclohexyl)-4-methoxybenzoic acid, 3-t-butyl-2-methoxy-5-methylbenzoic acid, 3-t-butyl-4-methoxy-5-methylbenzoic acid, 5-t-butyl-2-methoxy-3-methylbenzoic acid, 3-t-pentyl-4-methoxy-5-methylbenzoic acid, 3-t-octyl-4-methoxy-5-methylbenzoic acid, 3-cyclohexyl-4-methoxy-5-methylbenzoic acid, 3-(1-methylcyclohexyl)-4-methoxy-5-methylbenzoic acid, 3-t-butyl-4-methoxy-5-ethylbenzoic acids 3-t-pentyl-4-methoxy-5-ethylbenzoic acid, 3-t-octyl-4-methoxy-5-ethylbenzoic acid, 3-cyclohexyl-4-methoxy-5-ethylbenzoic acid, 3-(1-methylcyclohexyl)-4-methoxy-5-ethylbenzoic acid, 3,5-di-t-butyl-2-methoxybenzoic acid, 3,5-di-t-butyl-4-methoxybenzoic acid, 3-t-pentyl-4-methoxy-5-t-butylbenzoic acid, 3-t-octyl-4-methoxy-5-t-butylbenzoic acid, 3-cyclohexyl-4-methoxy-5-t-butylbenzoic acid, 3-(3-(1-methylcyclohexyl)-4-methoxy-5-t-butylbenzoic acid, 3-t-butyl-2-ethoxybenzoic acid, 3-t-butyl-4-ethoxybenzoic acid, 3-t-butyl-4-ethoxy-5-methylbenzoic acid, 3-t-butyl-2-ethoxy-5-methylbenzoic acid, 5-t-butyl-2-ethoxy-3-methylbenzoic acid, 3,5-di-t-butyl-4-ethoxybenzoic acid, 3,5-di-t-butyl-2-ethoxybenzoic acid, (3-t-butyl-2-hydroxyphenyl)acetic acid, (3-t-butyl-4-hydroxyphenyl)acetic acid, (5-t-butyl-2-hydroxyphenyl) acetic acid, (3-t-pentyl-4-hydroxyphenyl)acetic acid, (3-t-octyl-4-hydroxyphenyl)acetic acid, (3-cyclohexyl-4-hydroxyphenyl)acetic acid, [3-(1-methylcyclohexyl)-4-hydroxyphenyl]acetic acid, (3-t-butyl-2-hydroxy-5-methylphenyl)acetic acid, (3-t-butyl-4-hydroxy-5-methylphenyl)acetic acid, (5-t-butyl-2-hydroxy-3-methylphenyl)acetic acid, (3-t-pentyl-4-hydroxy-5-methylphenyl)acetic acid, (3-t-octyl-4-hydroxy-5-methylphenyl)acetic acid, (3-cyclohexyl-4-hydroxy-5-methylphenyl)acetic acid, [3-(1-methylcyclohexyl)-4-hydroxy-5-methylphenyl]acetic acid, (3-t-butyl-4-hydroxy-5-ethylphenyl)acetic acid, (3-t-pentyl-4-hydroxy-5-ethylphenyl)acetic acid, (3-t-octyl-4-hydroxy-5-ethylphenyl)acetic acid, (3-cyclohexyl-4-hydroxy-5-ethylphenyl)acetic acid, [3-(1-methylcyclohexyl)-4-hydroxy-5-ethylphenyl]acetic acid, (3,5-di-t-butyl-2-hydroxyphenyl)acetic acid, (3,5-di-t-butyl-4-hydroxyphenyl)acetic acid, (3-t-pentyl-4-hydroxy-5-t-butylphenyl)acetic acid, (3-t-octyl-4-hydroxy-5-t-butylphenyl)acetic acid, ( 3-cyclohexyl-4-hydroxy-5-t-butylphenyl)acetic acid, [3-(1-methylcyclohexyl)-4-hydroxy-5-t-butylphenyl]acetic acid, (3-t-butyl-2-methoxyphenyl)acetic acid, (3-t-butyl-4-methoxyphenyl) acetic acid, (3-t-butyl-5-methoxyphenyl)acetic acid, (3-t-pentyl-4-methoxyphenyl)acetic acid, (3-t-octyl-4-methoxyphenyl)acetic acid, (3-cyclohexyl-4-methoxyphenyl)acetic acid, [3-(1-methylcyclohexyl)-4-methoxyphenyl]acetic acid, (3-t-butyl-2-methoxy-5-methylphenyl)acetic acid, (3-t-butyl-4-methoxy-5-methylphenyl)acetic acid, (5-t-butyl-2-methoxy-3-methylphenyl)acetic acid, (3-t-pentyl-4-methoxy-5-methylphenyl)acetic acid, (3-t-octyl-4-methoxy-5-methylphenyl)acetic acid, (3-cyclohexyl-4-methoxy-5-methylphenyl)acetic acid, [3-(1-methylcyclohexyl)-4-methoxy-5-methylphenyl]acetic acid, (3-t-butyl-4-methoxy-5-ethylphenyl)acetic acid, (3-t-pentyl-4-methoxy-5-ethylphenyl)acetic acid, (3-t-octyl-4-methoxy-5-ethylphenyl)acetic acid, (3-cyclohexyl-4-methoxy-5-ethylphenyl)acetic acid, [3-(1-methylcyclohexyl)-4-methoxy-5-ethylphenyl]acetic acid, (3,5-di-t-butyl-2-methoxyphenyl)acetic acid, (3,5-di-t-butyl-4-methoxyphenyl)acetic acid, (3-t-pentyl-4-methoxy-5-t-butylphenyl)acetic acid, (3-t-octyl-4-methoxy-5-t-butylphenyl)acetic acid, (3-cyclohexyl-4-methoxy-5-t-butylphenyl)acetic acid, [3-(1-methylcyclohexyl)-4-methoxy-5-t-butylphenyl]acetic acid, (3-t-butyl-2-ethoxyphenyl)acetic acid, (3-t-butyl- 4-ethoxyphenyl)acetic acid, (3-t-butyl-4-ethoxy-5-ethylphenyl)acetic acid, (3-t-butyl-2-ethoxy-5-methylphenyl)acetic acid, (5-t-butyl-2-ethoxy-3-methylphenyl)acetic acid, (3,5-di-t-butyl-4-ethoxyphenyl)acetic acid, (3,5-di-t-butyl-2-ethoxyphenyl) acetic acid, 3-(3-t-butyl-2-hydroxyphenyl)propionic acid, 3-(3-t-butyl-4-hydroxyphenyl)propionic acid, 3-(5-t-butyl-2-hydroxyphenyl)propionic acid, 3-(3-t-pentyl-4-hydroxyphenyl)propionic acid, 3-(3-t-octyl-4-hydroxyphenyl)propionic acid, 3-(3-cyclohexyl-4-hydroxyphenyl)propionic acid, 3-[3-(1-methylcyclohexyl)-4-hydroxyphenyl]propionic acid, 3-(3-t-butyl-2-hydroxy-5-methylphenyl) propionic acid, 3-(3-t-butyl-4-hydroxy-5-methylphenyl) propionic acid, 3-(5-t-butyl-2-hydroxy-3-methylphenyl) propionic acid, 3-(3-t-pentyl-4-hydroxy-5-methylphenyl)propionic acid, 3-(3-t-octyl-4-hydroxy-5-methylphenyl)propionic acid, 3-(3-cyclohexyl-4-hydroxy-5-methylphenyl)propionic acid, 3-[3-(1-methylcyclohexyl)-4-hydroxy-5-methylphenyl]propionic acid, 3-(3-t-butyl-4-hydroxy-5-ethylphenyl) propionic acid, 3-(3-t-pentyl-4-hydroxy-5-ethylphenyl) propionic acid, 3-(3-t-octyl-4-hydroxy-5-ethylphenyl) propionic acid, 3-(3-cyclohexyl-4-hydroxy-5-ethylphenyl)propionic acid, 3-[3-(1-methylcyclohexyl)-4-hydroxy-5-ethylphenyl]propionic acid, 3-(3,5-di-t-butyl-2-hydroxyphenyl) propionic acid, 3-(3,5-di-t-butyl- 4-hydroxyphenyl) propionic acid, 3-(3-t-pentyl-4-hydroxy-5-t-butylphenyl) propionic acid, 3-(3-t-octyl-4-hydroxy-5-t-butylphenyl) propionic acid, 3-(3-cyclohexyl-4-hydroxy-5-t-butylphenyl)propionic acid, 3-[3-(1-methylcyclohexyl)-4-hydroxy-5-t-butylphenyl]propionic acid, 3-(3-t-butyl-2-methoxyphenyl) propionic acid, 3-(3-t-butyl-4-methoxyphenyl) propionic acid, 3-(3-t-butyl-5-methoxyphenyl) propionic acid, 3-(3-t-pentyl-4-methoxyphenyl) propionic acid, 3-(3-t-octyl-4-methoxyphenyl) propionic acid, 3-(3-cyclohexyl-4-methoxyphenyl)propionic acid, 3-[3-(1-methylcyclohexyl)-4-methoxyphenyl]propionic acid, 3-(3-t-butyl-2-methoxy-5-methylphenyl) propionic acid, 3-(3-t-butyl-4-methoxy-5-methylphenyl) propionic acid, 3-(5-t-butyl-2-methoxy-3-methylphenyl) propionic acid, 3-(3-t-pentyl-4-methoxy-5-methylphenyl) propionic acid, 3-(3-t-octyl-4-methoxy-5-methylphenyl) propionic acid, 3-(3-cyclohexyl-4-methoxy-5-methylphenyl)propionic acid, 3-[3-(1-methylcyclohexyl)-4-methoxy-5-methylphenyl]propionic acid, 3-(3-t-butyl-4-methoxy-5-ethylphenyl) propionic acid, 3-(3-t-pentyl-4-methoxy-5-ethylphenyl) propionic acid, 3-(3-t-octyl-4-methoxy-5-ethylphenyl) propionic acid, 3-(3-cyclohexyl-4-methoxy-5-ethylphenyl)propionic acid, 3-[3-(1-methylcyclohexyl)-4-methoxy-5-ethylphenyl]propionic acid, 3-(3,5-di-t-butyl-2-methoxyphenyl) propionic acid, 3-(3,5-di-t-butyl-4-methoxyphenyl) propionic acid, 3-(3-t-pentyl-4-methoxy-5-t-butylphenyl) propionic acid, 3-(3-t-octyl-4-methoxy-5-t-butylphenyl) propionic acid, 3-(3-cyclohexyl-4-methoxy-5-t-butylphenyl)propionic acid, 3-[3-(1-methylcyclohexyl)-4-methoxy-5-t-butylphenyl] propionic acid, 3-(3-t-butyl-2-ethoxyphenyl) proponic acid, 3-(3-t-butyl-4-ethoxyphenyl) propionic acid, 3-(3-t-butyl-4-ethoxy-5-methylphenyl) propionic acid, 3-(3-t-butyl-2-ethoxy-5-methylphenyl) propionic acid, 3-(5-t-butyl-2- ethoxy-3-methylphenyl) propionic acid, 3-(3,5-di-t-butyl-4-ethoxyphenyl) propionic acid, 3-(3,5-di-t-butyl-2-ethoxyphenyl) propionic acid, 3-(3-t-butyl-2-hydroxyphenyl) butanoic acid, 3-(3-t-butyl-4-hydroxyphenyl) butanoic acid, 3-(3-t-butyl-4-hydroxy-5-methylphenyl) butanoic acid, 3-(3-t-butyl-2-hydroxy-5-methylphenyl) butanoic acid, 3-(5-t-butyl-2-hydroxy-3-methylphenyl) butanoic acid, 3-(3,5-di-t-butyl-4-hydroxyphenyl) butanoic acid, 3-(3,5-di-t-butyl-2-hydroxyphenyl) butanoic acid, 3-(3-t-butyl-2-methoxyphenyl) butanoic acid, 3-(3-t-butyl-4-methoxyphenyl) butanoic acid, 3-(3-t-butyl-4-methoxy-5-methylphenyl) butanoic acid, 3-(3-t-butyl-2-methoxy-5-methylphenyl) butanoic acid, 3-(5-t-butyl-2-methoxy-3-methylphenyl) butanoic acid, 3-(3,5-di-t-butyl-4-methoxyphenyl) butanoic acid and 3-(3,5-di-t-butyl-2-methoxyphenyl) butanoic acid.

Such carboxylic acids can be produced, for example, by subjecting the corresponding hydroxybenzoic acid, alkoxybenzoic acid, aralkyloxybenzoic acid, etc. to the Friedel-Crafts reaction using a catalyst such as aluminum chloride or zinc chloride when A is a direct bond. When Z?? is a hydroxyl group, an alkoxy group or an aralkyloxy group, they can be produced, for example, by carrying out the Kolbe-Schmitt reaction using the corresponding phenols, alkali metals hydroxides such as sodium chloride, potassium chloride, and carbon dioxide according to the methods described in JP-A-62-61949 and JP-A-63-165341.

In addition, when A is an alkylene having 1 to 8 carbon atoms, the compounds can be produced by acylating the corresponding phenol using a Friedel-Crafts catalyst, such as aluminum chloride and zinc chloride, and carboalkoxyalkanoylhalogenoide, reducing a carbonyl group at the benzyl position with a hydrogenation catalyst such as carbon palladium, carbon platinum, etc. to convert into an alkylene and hydrolyzing an ester with an acid or alkali, according to the method described in Rubber Chemistry and Technology 46, 96(1973).

Examples of the hydroxyl compound (XII), when the connecting group X is a group of formula (V), include 2-hydroxyethyl benzoate, 2-hydroxyethyl 3-t-butyl-2-hydroxybenzoate, 2-hydroxyethyl 3-t-butyl-4-hydroxybenzoate, 2-hydroxyethyl 3-t-butyl-5-hydroxybenzoate, 2-hydroxyethyl 3-t-pentyl-4-hydroxybenzoate, 2-hydroxyethyl 3-t-octyl-4-hydroxybenzoate, 2-hydroxyethyl 3-cyclohexyl-4-hydroxybenzoate, 2-hydroxyethyl 3-(1-methylcyclohexyl)-4-hydroxybenzoate, 2-hydroxyethyl 3-t-butyl-2-hydroxy-5-methylbenzoate, 2-hydroxyethyl 3-t-butyl-4-hydroxy-5-methylbenzoate, 3-hydroxypropyl 3-t-butyl-4-hydroxy-5-methylbenzoate, 4-hydroxybutyl 3-t-butyl-4-hydroxy-5-methylbenzoate, 2-hydroxyethyl 5-t-butyl-2-hydroxy-3-methylbenzoate, 2-hydroxyethyl 3-t-pentyl-4-hydroxy-5-methylbenzoate, 2-hydroxyethyl 3-t-octyl-4-hydroxy-5-methylbenzoate, 2-hydroxyethyl 3-cyclohexyl-4-hydroxy-5-methylbenzoate, 2-hydroxyethyl 3-(1-methylcyclohexyl)-4-hydroxy-5-methylbenzoate, 2-hydroxyethyl 3-t-butyl-4-hydroxy-5-ethylbenzoate, 2-hydroxyethyl 3-t-pentyl-4-hydroxy-5-ethylbenzoate, 2-hydroxyethyl 3-t-octyl-4-hydroxy-5-ethylbenzoate, 2-hydroxyethyl 3-cyclohexyl-4-hydroxy-5-ethylbenzoate, 2-hydroxyethyl 3-(1-methylcyclohexyl)-4-hydroxy-5-ethylbenzoate, 2-hydroxyethyl 3,5-di-t-butyl-2-hydroxybenzoate, 2-hydroxyethyl 3,5-di-t-butyl-4-hydroxybenzoate, 3-hydroxypropyl 3,5-di-t-butyl-4-hydroxybenzoate, 4-hydroxybutyl 3,5-di-t-butyl-4-hydroxybenzoate, 2-hydroxyethyl 3-t-pentyl-4-hydroxy-5-t-butylbenzoate, 2-hydroxyethyl 3-t-octyl-4-hydroxy-5-t-butylbenzoate, 2-hydroxyethyl 3-cyclohexyl-4-hydroxy-5-t-butylbenzoate, 2-hydroxyethyl 3-(3-(1-methylcyclohexyl)-4-hydroxy-5-t-butylbenzoate, 2-hydroxyethyl (3-t-butyl-4-hydroxyphenyl)acetate, 2-hydroxyethyl (3-t-butyl-5-hydroxyphenyl)acetate, 2-hydroxyethyl (3-t-pentyl-4-hydroxyphenyl)acetate, 2-hydroxyethyl (3-t-octyl-4-hydroxyphenyl)acetate, 2-hydroxyethyl (3-cyclohexyl-4-hydroxyphenyl)acetate, 2-hydroxyethyl [3-(1-methylcyclohexyl)-4-hydroxyphenyl]acetate, 2-hydroxyethyl (3-t-butyl-2-hydroxy-5-methylphenyl)acetate, 2-hydroxyethyl (3-t-butyl-4-hydroxy-5-methylphenyl)acetate, 3-hydroxypropyl (3-t-butyl-4-hydroxy-5-methylphenyl)acetate, 4-hydroxybutyl (3-t-butyl-4-hydroxy-5-methylphenyl)acetate, 2-hydroxyethyl (5-t-butyl-2-hydroxy-3-methylphenyl)acetate, 2-hydroxyethyl (3-t-pentyl-4-hydroxy-5-methylphenyl)acetate, 2-hydroxyethyl (3-t-octyl-4-hydroxy-5-methylphenyl)acetate, 2-hydroxyethyl (3-cyclohexyl-4-hydroxy-5-methylphenyl)acetate, 2-hydroxyethyl [3-(1-methylcyclohexyl)-4-hydroxy-5-methylphenyl)acetate, 2-hydroxyethyl (3-t-butyl-4-hydroxy-5-ethylphenyl)acetate, 2-hydroxyethyl (3-t-pentyl-4-hydroxy-5-ethylphenyl) acetate, 2-hydroxyethyl (3-t-octyl-4-hydroxy-5-ethylphenyl)acetate, 2-hydroxyethyl (3-cyclohexyl-4-hydroxy-5-ethylphenyl)acetate, 2-hydroxyethyl [3-(1-methylcyclohexyl)-4-hydroxy-5-ethylphenyl)acetate, 2-hydroxyethyl (3,5-di-t-butyl-2-hydroxyphenyl)acetate, 2-hydroxyethyl (3,5-di-t-butyl-4-hydroxyphenyl)acetate, 3-hydroxypropyl (3,5-di-t-butyl-4-hydroxyphenyl)acetate, 4-hydroxybutyl (3,5-di-t-butyl-4-hydroxyphenyl)acetate, 2-hydroxyethyl (3-t-pentyl-4-hydroxy-5-t-butylphenyl) acetate, 2-hydroxyethyl (3-t-octyl-4-hydroxy-5-t-butylphenyl)acetate, 2-hydroxyethyl (3-cyclohexyl-4-methoxy-5-t-butylphenyl)acetate, 2-hydroxyethyl [3-(1-methylcyclohexyl)-4-hydroxy-5-t-butylphenyl]acetate, 2-hydroxyethyl 3-(3-t-butyl-2-hydroxyphenyl)propionate, 2-hydroxyethyl 3-(3-t-butyl-4-hydroxyphenyl)propionate, 2-hydroxyethyl 3-(3-t-butyl-5-hydroxyphenyl)propionate, 2-hydroxyethyl 2-,(3-t-pentyl-4-hydroxyphenyl)propionate, 2-hydroxyethyl 3-(3-t-octyl-4-hydroxyphenyl)propionate, 2-hydroxyethyl 3-(3-t-cyclohexyl-4-hydroxyphenyl) propionate, 2-hydroxyethyl 3-[3-(1-methylcyclohexyl)-4-hydroxyphenyl]propionate, 2-hydroxyethyl 3-(3-t-butyl-2-hydroxy-5-methylphenyl)propionate, 2-hydroxyethyl 3-(3-t-butyl-4-hydroxy-5-methylphenyl)propionate, 3-hydroxybutyl 3-(3-t-butyl-4-hydroxy-5-methylphenyl) propionate, 4-hydroxybutyl 3-(3-t-butyl-4-hydroxy-5-methylphenyl)propionate, 2-hydroxyethyl 3-(5-t-butyl-2-hydroxy-3-methylphenyl)propionate, 2-hydroxyethyl (3-t-pentyl-4-hydroxy-5-methylphenyl)propionate, 2-hydroxyethyl 3-(3-t-octyl-4-hydroxy-5-methylphenyl)propionate, 2-hydroxyethyl 3-(3-cyclohexyl-4-hydroxy-5-methylphenyl)propionate, 2-hydroxyethyl 3-[3-(1-methylcyclohexyl)-4-hydroxy-5-methylphenyl]propionate, 2-hydroxyethyl 3-(3-t-butyl-4-hydroxy-5-ethylphenyl) propionate, 2-hydroxyethyl 3-(3-t-pentyl-4-hydroxy-5-ethylphenyl)propionate, 2-hydroxyethyl 3-(3-t-octyl-4-hydroxy-5-ethylphenyl)propionate, 2-hydroxyethyl 3-(3-cyclohexyl-4-hydroxy-5-ethylphenyl)propionate, 2-hydroxyethyl 3-[3-(1-methylcyclohexyl)-4-hydroxy-5-ethylphenyl]propionate, 2-hydroxyethyl 3-(3,5-di-t-butyl-2-hydroxyphenyl)propionate, 2-hydroxyethyl 3-(3,5-di-t-butyl-4-hydroxyphenyl)propionate, 3-hydroxypropyl 3-(3,5-di-t-butyl-4-hydroxyphenyl)propionate, 4-hydroxybutyl 3-(3,5-di-t-butyl-4-hydroxyphenyl)propionate, 2-hydroxyethyl 3-(3-t-pentyl-4-hydroxy-5-t-butylphenyl)

propionate, 2-hydroxyethyl 3-(3-t-octyl-4-hydroxy-5-t-butylphenyl)propionate, 2-hydroxyethyl 3-(3-cyclohexyl-4-hydroxy-5-t-butylphenyl)propionate, 2-hydroxyethyl 3-[3-(1-methylcyclohexyl)-4-hydroxy-5-t-butylphenyl]propionate, 2-hydroxyethyl 4-(3-t-butyl-2-hydroxyphenyl)butyrate, 2-hydroxyethyl 4-(3-t-butyl-4-hydroxyphenyl)butyrate, 2-hydroxyethyl 4-(3-t-butyl-4-hydroxy-5-methylphenyl)butyrate, 3-hydroxypropyl 4-(3-t-butyl-4-hydroxy-5-methylphenyl)butyrate, 4-hydroxybutyl 4-(3-t-butyl-4-hydroxy-5-methylphenyl)butyrate, 2-hydroxyethyl 4-(3-t-butyl-2-hydroxy-5-methylphenyl)butyrate, 2-hydroxyethyl 4-(5-t-butyl-2-hydroxy- 3-methylphenyl)butyrate, 2-hydroxyethyl 4-(3,5-di-t-butyl-4-hydroxyphenyl)butyrate, 3-hydroxypropyl 4-(3,5-di-t-butyl-4-hydroxyphenyl)butyrate, 4-hydroxybutyl 4-(3,5-di-t-butyl-4-hydroxyphenyl)butyrate, 2-hydroxyethyl 4-(3,5-di-t-butyl-4-hydroxyphenyl)butyrate, 2-hydroxyethyl 3-t-butyl-2-methoxybenzoate, 2-hydroxyethyl 3-t-butyl-4-methoxybenzoate, 2-hydroxyethyl 3-t-butyl-5-methoxybenzoate, 2-hydroxyethyl 3-t-pentyl-4-methoxybenzoate, 2-hydroxyethyl 3-t-octyl-4-methoxybenzoate, 2-hydroxyethyl 3-cyclohexyl-4-methoxybenzoate, 2-hydroxyethyl 3-(1-methylcyclohexyl)-4-methoxybenzoate, 2-hydroxyethyl 3-t-butyl-2-methoxy-5-methylbenzoate, 2-hydroxyethyl 3-t-butyl-4-methoxy-5-methylbenzoate, 3-hydroxypropyl 3-t-butyl-4-methoxy-5-methylbenzoate, 4-hydroxybutyl 3-t-butyl-4-methoxy-5-methylbenzoate, 2-hydroxyethyl 5-t-butyl-2-methoxy-3-methylbenzoate, 2-hydroxyethyl 3-t-pentyl-4-methoxy-5-methylbenzoate, 2-hydroxyethyl 3-t-octyl-4-methoxy-5-methylbenzoate, 2-hydroxyethyl 3-cyclohexyl-4-methoxy-5-methylbenzoate, 2-hydroxyethyl 3-(1-methylcyclohexyl)-4-methoxy-5-methylbenzoate, 2-hydroxyethyl 3-t-butyl-4-methoxy-5-ethylbenzoate, 2-hydroxyethyl 3-t-pentyl-4-methoxy-5-ethylbenzoate, 2-hydroxyethyl 3-t-octyl-4-methoxy-5-ethylbenzoate, 2-hydroxyethyl 3-cyclohexyl-4-methoxy-5-ethylbenzoate, 2-hydroxyethyl 3-(1-methylcyclohexyl)-4-methoxy-5-ethylbenzoate, 2-hydroxyethyl 3,5-di-t-butyl- 2-methoxybenzoate, 2-hydroxyethyl 3.5-di-t-butyl-4-methoxybenzoate, 3-hydroxypropyl 3,5-di-t-butyl-4-methoxybenzoate, 4-hydroxybutyl 3,5-di-t-butyl-4-methoxybenzoate, 2-hydroxyethyl 3-t-pentyl-4-methoxy-5-t-butylbenzoate, 2-hydroxyethyl 3-t-octyl-4-methoxy-5-t-butylbenzoate, 2-hydroxyethyl 3-cyclohexyl-4-methoxy-5-t-butylbenzoate, 2-hydroxyethyl 3-(3-(1-methylcyclohexyl)-4-methoxy-5-t-butylbenzoate, 2-hydroxyethyl 3-t-butyl-2-ethoxybenzoate, 2-hydroxyethyl 3-t-butyl-4-ethoxybenzoate, 2-hydroxyethyl 3-t-butyl-4-ethoxy-5-methylbenzoate, 3-hydroxypropyl 3-t-butyl-4-ethoxy-5-methylbenzoate, 4-hydroxybutyl 3-t-butyl-4-ethoxy-5-methylbenzoate, 2-hydroxyethyl 3-t-butyl-2-ethoxy-5-methylbenzoate, 2-hydroxyethyl 5-t-butyl-2-ethoxy-3-methylbenzoate, 2-hydroxyethyl 3,5-di-t-butyl-4-ethoxybenzoate, 2-hydroxyethyl 3,5-di-t-butyl-2-ethoxybenzoate, 2-hydroxyethyl (3-t-butyl-4-methoxyphenyl)acetate, 2-hydroxyethyl (3-t-butyl-5-methoxyphenyl)acetate, 2-hydroxyethyl (3-t-pentyl-4-methoxyphenyl)acetate, 2-hydroxyethyl (3-t-octyl-4-methoxyphenyl)acetate, 2-hydroxyethyl (3-cyclohexyl-4-methoxyphenyl)acetate, 2-hydroxyethyl [3-(1-methylcyclohexyl)-4-methoxyphenyl]acetate, 2-hydroxyethyl (3-t-butyl-2-methoxy-5-methylphenyl)acetate, 2-hydroxyethyl 3-(3-t-butyl-4-methoxy-5-methylphenyl)acetate, 3-hydroxypropyl (3-t-butyl-4-methoxy-5-methylphenyl)acetate, 4-hydroxybutyl (3-t-butyl-4-methoxy-5-methylphenyl)acetate, 2-hydroxyethyl (5-t-butyl-2-methoxy-3-methylphenyl)acetate, 2-hydroxyethyl (3-t-pentyl-4-methoxy-5-methylphenyl)acetate, 2-hydroxyethyl (3-t-octyl-4-methoxy-5-methylphenyl)acetate, 2-hydroxyethyl (3-cyclohexyl-4-methoxy-5-methylphenyl)acetate, 2-hydroxyethyl [3-(1-methylcyclohexyl)-4-methoxy-5-methylphenyl]acetate, 2-hydroxyethyl (3-t-butyl-4-methoxy-5-ethylphenyl)acetate, 2-hydroxyethyl (3-t-pentyl-4-methoxy-5-ethylphenyl)acetate, 2-hydroxyethyl (3-t-octyl-4-methoxy-5-ethylphenyl) acetate, 2-hydroxyethyl (3-cyclohexyl-4-methoxy-5-ethylphenyl)acetate, 2-hydroxyethyl [3-(1-methylcyclohexyl)-4-methoxy-5-ethylphenyl]acetate, 2-hydroxyethyl (3,5-di-t-butyl-2-methoxyphenyl)acetate, 2-hydroxyethyl (3,5-di-t-butyl-4-methoxyphenyl)acetate, 3-hydroxypropyl (3,5-di-t-butyl-4-methoxyphenyl)acetate, 4-hydroxybutyl (3,5-di-t-butyl-4-methoxyphenyl)acetate, 2-hydroxyethyl (3-t-pentyl-4-methoxy-5-t-butylphenyl)acetate, 2-hydroxyethyl (3-t-octyl-4-hydroxy-5-t-butylphenyl)acetate, 2-hydroxyethyl (3-cyclohexyl-4-hydroxy-5-t-butylphenyl)acetate, 2-hydroxyethyl [3-(1-methylcyclohexyl)-4-methoxy-5-t-butylphenyl]acetate, 2-hydroxyethyl (3-t-butyl-2-ethoxyphenyl)acetate, 2-hydroxyethyl (3-t-butyl-4-ethoxyphenyl)acetate, 2-hydroxyethyl (3-t-butyl-4-ethoxy-5-methylphenyl)acetate, 3-hydroxypropyl (3-t-butyl-4-ethoxy-5-methylphenyl)acetate, 4-hydroxybutyl (3-t-butyl-4-ethoxy-5-methylphenyl)acetate, 2-hydroxyethyl (3-t-butyl-2-ethoxy-5-methylphenyl)acetate, 2-hydroxyethyl (3-t-butyl-2-ethoxy-5-methylphenyl)acetate, 2-hydroxyethyl (5-t-butyl-2-ethoxy-3-methylphenyl)acetate, 2-hydroxyethyl (3,5-di-t-butyl-4-ethoxyphenyl)acetate, 3-hydroxypropyl (3,5-di-t-butyl-4-ethoxyphenyl)acetate, 4-hydroxybutyl (3,5-di-t-butyl-4-ethoxyphenyl)acetate, 2-hydroxyethyl (3,5-di-t-butyl-2-ethoxyphenyl)acetate, 2-hydroxyethyl 3-(3-t-butyl-2-methoxyphenyl)propionate, 2-hydroxyethyl 3-(3-t-butyl-4-methoxyphenyl)propionate, 2-hydroxyethyl 3-(3-t-butyl-5-methoxyphenyl)propionate, 2-hydroxyethyl 2-(3-t-pentyl-4-methoxyphenyl)propionate, 2-hydroxyethyl 3-(3-t-octyl-4-methoxyphenyl)propionate, 2-hydroxyethyl 3-(3-cyclohexyl-4-methoxyphenyl)propionate, 2-hydroxyethyl 3-[3-(1-methylcyclohexyl)-4-methoxyphenyl]propionate, 2-hydroxyethyl 3-(3-t-butyl-2-methoxy-5-methylphenyl) propionate, 2-hydroxyethyl 3-(3-t-butyl-4-methoxy-5-methylphenyl) propionate, 3-hydroxybutyl 3-(3-t-butyl-4-methoxy-5-methylphenyl)propionate, 4-hydroxybutyl 3-(3-t-butyl-4-methoxy-5-methylphenyl)propionate, 2-hydroxyethyl 3-(5-t-butyl-4-methoxy-3-methylphenyl)propionate, 2-hydroxyethyl 3-(3-t-pentyl-4-methoxy-5-methylphenyl)propionate, 2-hydroxyethyl 3-(3-t-octyl-4-methoxy-5-methylphenyl)propionate, 2-hydroxyethyl 3-(3-cyclohexyl-4-methoxy-5-methylphenyl)propionate, 2-hydroxyethyl 3-[3-(1-methylcyclohexyl)-4-methoxy- 5-methylphenyl]propionate, 2-hydroxyethyl 3-(3-t-butyl-4-methoxy-5-ethylphenyl)propionate, 2-hydroxyethyl 3-(3-t-pentyl-4-methoxy-5-ethylphenyl)propionate, 2-hydroxyethyl 3-(3-t-octyl-4-methoxy-5-ethylphenyl)propionate, 2-hydroxyethyl 3-(3-cyclohexyl-4-methoxy-5-ethylphenyl)propionate, 2-hydroxyethyl 3-[3-(1-methylcyclohexyl)-4-methoxy-5-ethylphenyl]propionate, 2-hydroxyethyl 3-(3,5-di-t-butyl-2-methoxyphenyl) propionate, 2-hydroxyethyl 3-(3,5-di-t-butyl-4-methoxyphenyl) propionate, 3-hydroxypropyl 3-(3, 5-di-t-butyl-4-methoxyphenyl) propionate, 4-hydroxybutyl 3-(3,5-di-t-butyl-4-methoxyphenyl) propionate, 2-hydroxyethyl 3-(3-t-pentyl-4-methoxy-5-t-butylphenyl) propionate, 2-hydroxyethyl 3-(3-t-octyl-4-methoxy-5-t-butylphenyl) propionate, 2-hydroxyethyl 3-(3-cyclohexyl-4-methoxy-5-t-butylphenyl)propionate, 2-hydroxyethyl 3-[3-

(1-methylcyclohexyl)-4-methoxy-5-t-butylphenyl] propionate, 2-hydroxyethyl 3-(3-t-butyl-2-ethoxyphenyl) propionate, 2-hydroxyethyl 3-(3-t-butyl-4-ethoxyphenyl) propionate, 2-hydroxyethyl 3-(3-t-butyl-4-ethoxy-5-methylphenyl) propionate, 3-hydroxypropyl 3-(3-t-butyl-4-ethoxy-5-methylphenyl) propionate, 4-hydroxybutyl 3-(3-t-butyl-2-ethoxy-5-methylphenyl) propionate, 2-hydroxyethyl 3-(5-t-butyl-2-ethoxy-3-methylphenyl) propionate, 2-hydroxyethyl 3-(3,5-di-t-butyl-4-ethoxyphenyl) propionate, 3-hydroxypropyl 3-(3,5-di-t-butyl-4-ethoxyphenyl) propionate, 4-hydroxybutyl 3-(3,5-di-t-butyl-4-ethoxyphenyl)propionate, 2-hydroxyethyl 3-(3,5-di-t-butyl-2-ethoxyphenyl)propionate, 2-hydroxyethyl 4-(3-t-butyl-2-methoxylphenyl) butyrate, 2-hydroxyethyl 4-(3-t-butyl-4-methoxyphenyl) butyrate, 2-hydroxyethyl 4-(3-t-butyl-4-methoxy-5-methylphenyl) butyrate, 3-hydroxypropyl 4-(3-t-butyl-4-methoxy-5-methylphenyl) butyrate, 4-hydroxybutyl 4-(3-t-butyl-4-methoxy-5-methyliphenyl) butyrate, 2-hydroxyethyl 4-(3-t-butyl-2-methoxy-5-methylphenyl) butyrate, 2-hydroxyethyl 4-(5-t-butyl-2-methoxy-3-methylphenyl) butyrate, 2-hydroxyethyl 4-(3,5-di-t-butyl-4-methoxyphenyl)butyrate, 3-hydroxypropyl 4-(3,5-di-t-butyl-4-methoxyphenyl) butyrate, 4-hydroxybutyl 4-(3,5-di-t-butyl-4-methoxyphenyl)butyrate, 2-hydroxyethyl 4-(3,5-di-t-butyl-2-methoxyphenyl) butyrate, 2-hydroxyethyl 4-(3-t-butyl-4-ethoxy-5-methylphenyl) butyrate, 3-hydroxypropyl 4-(3-t-butyl-4-ethoxy-5-methylphenyl) butyrate, 4-hydroxybutyl 4-(3-t-butyl-4-ethoxy-5-methylphenyl) butyrate, 2-hydroxyethyl 4-(3,5-di-t-butyl-4-ethoxyphenyl) butyrate, 3-hydroxypropyl 4-(3,5-di-t-butyl-4-ethoxyphenyl) butyrate, and 4-hydroxybutyl 4-(3,5-di-t-butyl-4-ethoxyphenyl) butyrate.

These compounds can be produced, for example, by reacting the corresponding diol with the corresponding carboxylic acid, carboxylate, halide carboxylate, etc.

Examples of the hydroxyl compound (XII), when the connecting group X is a group of the formula (VI), include phenyl hydroxyacetate, benzyl hydroxyacetate, phenyl 2-hydroxypropionate, benzyl 2-hydroxypropionate, phenyl 3-hydroxypropionate, benzyl 3-hydroxypropionate, phenyl 2-hydroxy-2-methylpropionate, benzyl 2-hydroxy-2-methylpropionate, phenyl 3-hydroxy-2-methylpropionate, benzyl 3-hydroxy-2-methylpropionate, phenyl 2-hydroxybutyrate, benzyl 2-hydroxybutyrate, phenyl 2-hydroxy-2-methylbutyrate, benzyl 2-hydroxy-2-methylbutyrate, phenyl 2-hydroxy-3-methylbutyrate, benzyl 2-hydroxy-3-methylbutyrate, phenyl 2-ethyl-2-hydroxybutyrate, benzyl 2-ethyl-2-hydroxybutyrate, phenyl 3-hydroxybutyrate, benzyl 3-hydroxybutyrate, phenyl 4-hydroxybutyrate, benzyl 4-hydroxybutyrate, phenyl 2-hydroxy-4-methylpentanoate, benzyl 2-hydroxy-4-methylpentanoate, phenyl 2-hydroxyhexanoate and benzyl 2-hydroxyhexanoate.

Examples of the hydroxyl compound (XII), when the connecting group X is a group of the formula (VII), include 2-[N-(3-t-butyl-2-hydroxyphenylmethyl)amino]ethanol, 2-[N-(3-t-butyl-4-hydroxyphenylmethyl)amino]ethanol, 2-[N-(3-t-butyl-2-hydroxy-5-methylphenylmethyl)amino]ethanol, 2-[N-(3,5-di-t-butyl-2-hydroxyphenylmethyl)amino]ethanol, 2-[N-(3-t-butyl-4-hydroxy-5-methylphenylmethyl)amino]ethanol, 2-[N-(3,5-di-t-butyl-4-hydroxyphenylmethyl)amino]ethanol, 2-[N-(2-methyl-3,5-di-t-butyl-4-hydroxyphenylmethyl)amino]ethanol, 2-[N-(3-t-butyl-2-methoxyphenylmethyl)amino]ethanol, 2-[N-(3-t-butyl-4-methoxyphenylmethyl)amino]ethanol, 2-[N-( 3-t-butyl-2-methoxy-5-methylphenylmethyl)amino]ethanol, 2-[N-(3,5-di-t-butyl-2-methoxyphenylmethyl)amino]ethanol, 2-[N-(3-t-butyl-4-methoxy-5-methylphenylmethyl)amino]ethanol, 2-[N-(3,5-di-t-butyl-4-methoxyphenylmethyl)amino]ethanol, 2-[N-(2-methyl-3,5-di-t-butyl-4-methoxyphenylmethyl)amino]ethanol, 2-[N-(3-t-butyl-2-hydroxyphenylmethyl)-N-methylamino]ethanol, 2-[N-(3-t-butyl-4-hydroxyphenylmethyl)-N-methylamino]ethanol, 2-[N-(3-t-butyl-2-hydroxy-5-methylphenylmethyl)-N-methylamino]ethanol, 2-[N-(3,5-di-t-butyl-2-hydroxyphenylmethyl)-N-methylamino]ethanol, 2-[N-(3-t-butyl-4-hydroxy-5-methylphenylmethyl)-N-methylamino]ethanol, 2-[N-(3,5-di-t-butyl-4-hydroxyphenylmethyl)-N-methylamino]ethanol, 2-[N-(2-methyl-3,5-di-t-butyl-4-hydroxyphenylmethyl)-N-methylamino]ethanol, 2-[N-(3-t-butyl-2-hydroxyphenylmethyl)-N-ethylamino]ethanol, 2-[N-(3-t-butyl-4-hydroxyphenylmethyl)-N-ethylamino]ethanol, 2-[N-(3-t-butyl-2-hydroxy-5-methylphenylmethyl)-N-ethylamino]ethanol, 2-[N-(3,5-di-t-butyl-2-hydroxyphenylmethyl)-N-ethylaminolethanol, 2-[N-(3-t-butyl-4-hydroxy-5-methylphenylmethyl)-N-ethylamino]ethanol, 2-[N-(3,5-di-t-butyl-4-hydroxyphenylmethyl)-N-ethylamino]ethanol, 2-[N-(2-methyl-3,5-di-t-butyl-4-hydroxyphenylmethyl)-N-ethylamino]ethanol, 2-[N-(3-t-butyl-2-hydroxyphenylmethyl)-N-t-butylamino]ethanol, 2-[N-(3-t-butyl-4-hydroxyphenylmethyl)-N-t-butylamino]ethanol, 2-[N-(3-t-butyl-2-hydroxy-5-methylphenylmethyl)-N-t-butylamino]ethanol, 2-[N-(3,5-di-t-butyl-2-hydroxyphenylmethyl)-N-t-butylamino]ethanol, 2-[N-(3-t-butyl-4-hydroxy-5-methylphenylmethyl)-N-t-butylamino]ethanol, 2-[N-(3,5-di-t-butyl-4-hydroxyphenylmethyl)-N-t-butylamino]ethanol, 2-[N-(2-methyl-3,5-di-t-butyl-4-hydroxyphenylmethyl)-N-t-butylamino]ethanol, 3-[N-(3-t-butyl-2-hydroxyphenylmethyl) amino]propanol, 3-[N-(3-t-butyl-4-hydroxyphenylmethyl)amino]propanol, 3-[N-(3-t-butyl-2-hydroxy-5-methylphenylmethyl)amino]propanol, 3-[N-(3,5-di-t-butyl-2-hydroxyphenylmethyl)amino]propanol, 3-[N-(3-t-butyl-4-hydroxy-5-methylphenylmethyl)amino]propanol, 3-[N-(3,5-di-t-butyl-4-hydroxyphenylmethyl)amino]propanol, 3-[N-(2-methyl-3,5-di-t-butyl-4-hydroxyphenylmethyl)amino]propanol, 3-[N-(3-t-butyl-2-hydroxy-5-methylphenylmethyl)-N-methylamino]propanol, 3-[N-(3,5-di-t-butyl-2-hydroxyphenylmethyl)-N-methylamino]propanol, 3-[N-(3-t-butyl-4-hydroxy-5-methylphenylmethyl)-N-methylamino]propanol, 3-[N-(3,5-di-t-butyl-4-hydroxyphenylmethyl)-N-methylamino]propanol, 4-[N-(3-t-butyl-2-hydroxyphenylmethyl)amino]butanol, 4-[N-(3-t-butyl-4-hydroxyphenylmethyl)amino]butanol, 4-[N-(3-t-butyl-2-hydroxy-5-methylphenylmethyl)amino]butanol, 4-[N-(3,5-di-t-butyl-2-hydroxyphenylmethyl)amino]butanol, 4-[N-(3-t-butyl-4-hydroxy-5-methylphenylmethyl)amino]butanol, 4-[N-(3,5-di-t-butyl- 4-hydroxyphenylmethyl)amino]butanol, 4-[N-(2-methyl-3,5-di-t-butyl-4-hydroxyphenylmethyl)amino]butanol, 4-[N-(3-t-butyl-2-hydroxy-5-methylphenylmethyl)-N-methylamino]butanol, 4-[N-(3,5-di-t-butyl-2-hydroxyphenylmethyl)-N-methylamino]butanol, 4-[N-(3-t-butyl-4-hydroxy-5-methylphenylmethyl)-N-t-methylamino]butanol and 4-[N-(3,5-di-t-butyl-4-hydroxyphenylmethyl)-N-methylamino]butanol.

When A is methylene, these compounds can be produced, for example, by reacting the corresponding alkanolamine with the corresponding phenol compound and formaldehyde. When A is an alkylene other than methylene, the compounds can be produced by reacting the corresponding alkanolamine with the corresponding halide.

Examples of the hydroxyl compound (XII), when the connecting group X is a group of the formula (VIII), include N-(2-hydroxyethyl)-2-hydroxy-3-t-butylbenzamide, N-(2-hydroxyethyl)-4-hydroxy-3-t-butylbenzamide, N-(2-hydroxyethyl)-2-hydroxy-3-t-butyl-5-methylbenzamide, N-(2-hydroxyethyl)-4-hydroxy-3-t-butyl-5-methylbenzamide, N-(2-hydroxyethyl)-2-hydroxy-3,5-di-t-butylbenzamide, N-(2-hydroxyethyl)-4-hydroxy-3,5-di-t-butylbenzamide, N-(2-hydroxyethyl)-3-(2-hydroxy-3-t-butylphenyl)propionamide, N-(2-hydroxyethyl)-3-(4-hydroxy-3-t-butylphenyl)propionamide, N-(2-hydroxyethyl)-3-(2-hydroxy-3-t-butyl-5-methylphenyl)propionamide, N-(2-hydroxyethyl)-3-(4-hydroxy-3-t-butyl-5-methylphenyl)propionamide, N-(2-hydroxyethyl)-3-(2-hydroxy-3,5-di-t-butylphenyl)propionamide, N-(2-hydroxyethyl)-3-(4-hydroxy-3,5-di-t-butylphenyl)propionamide, N-methyl-N-(2-hydroxyethyl)-3-(2-hydroxy-3-t-butylphenyl)propionamide, N-methyl-N-(2-hydroxyethyl)-3-(4-hydroxy-3-t-butylphenyl)propionamide, N-methyl-N-(2-hydroxyethyl)-3-(2-hydroxy-3-t-butyl-5-methylphenyl)propionamide, N-methyl-N-(2-hydroxyethyl)-3-(4-hydroxy-3-t-butyl-5-methylphenyl)propionamide, N-methyl-N-(2-hydroxyethyl)-3-(2-hydroxy-3,5-di-t-butylphenyl)propionamide, N-methyl-N-(2-hydroxyethyl)-3-(4-hydroxy-3,5-di-t-butylphenyl)propionamide, N-ethyl-N-(2-hydroxyethyl)-3-(2-hydroxy-3-t-butylphenyl)propionamide, N-ethyl-N-(2-hydroxyethyl)-3-(4-hydroxy-3-t-butylphenyl)propionamide, N-ethyl-N-(2-hydroxyethyl)-3-(2-hydroxy-3-t-butyl-5-methylphenyl)propionamide, N-ethyl-N-(2-hydroxyethyl)-3-(4-hydroxy-3-t-butyl-5-methylphenyl)propionamide, N-ethyl-N-(2-hydroxyethyl)-3-(2-hydroxy-3,5-di-t-butylphenyl)propionamide, N-ethyl-N-(2-hydroxyethyl)-3-(4-hydroxy-3,5-di-t-butylphenyl)propionamide, N-t-butyl-N-(2-hydroxyethyl)-3-(2-hydroxy-3-t-butylphenyl)propionamide, N-t-butyl-N-(2-hydroxyethyl)-3-(4-hydroxy-3-t-butylphenyl)propionamide, N-t-butyl-N-(2-hydroxyethyl)-3-(2-hydroxy-3-t-butyl-5-methylphenyl)propionamide, N-t-butyl-N-(2-hydroxyethyl)-3-(4-hydroxy-3-t-butyl-5-methylphenyl)propionamide, N-t-butyl-N-(2-hydroxyethyl)-3-(2-hydroxy-3,5-di-t-butylphenyl)propionamide, N-t-butyl-N-(2-hydroxyethyl)-3-(4-hydroxy-3,5-di-t-butylphenyl)propionamide, N-(3-hydroxypropyl)-3-(2-hydroxy-3-t-butylphenyl)propionamide, N-(3-hydroxypropyl)-3-(4-hydroxy-3-t-butylphenyl)propionamide, N-(3-hydroxypropyl)-3-(2-hydroxy-3-t-butyl-5-methylphenyl)propionamide, N-(3-hydroxypropyl)-3-(4-hydroxy-3-t-butyl-5-methylphenyl)propionamide, N-(3-hydroxypropyl)-3-(2-hydroxy-3,5-di-t-butylphenyl)propionamide, N-(3-hydroxypropyl)-3-(4-hydroxy-3,5-di-t-butylphenyl)propionamide, N-(4-hydroxybutyl)-3-(2-hydroxy-3-t-butylphenyl)propionamide, N-(4-hydroxybutyl)-3-(4-hydroxy-3-t-butylphenyl)propionamide, N-(4-hydroxybutyl)-3-(2-hydroxy-3-t-butyl-5-methylphenyl)propionamide, N-(4-hydroxybutyl)-3-(4-hydroxy-3-t-butyl-5-methylphenyl)propionamide, N-(4-hydroxybutyl)-3-(2-hydroxy-3,5-di-t-butylphenyl)propionamide, N-(4-hydroxybutyl)-3-(4-hydroxy-3,5-di-t-butylphenyl)propionamide, N-(6-hydroxyhexyl)-3-(2-hydroxy-3-t-butylphenyl)propionamide, N-(6-hydroxyhexyl)-3-(4-hydroxy-3-t-butylphenyl)propionamide, N-(6-hydroxyhexyl)-3-(2-hydroxy-3-t-butyl-5-methylphenyl)propionamide, N-(6-hydroxyhexyl)-3-(4-hydroxy-3-t-butyl-5-methylphenyl)propionamide, N-(6-hydroxyhexyl)-3-(2-hydroxy-3,5-di-t-butylphenyl)propionamide, N-(6-hydroxyhexyl)-3-(4-hydroxy-3,5-di-t-butylphenyl)propionamide, N-[1-(hydroxymethyl)-1-methyl-2-hydroxyethyl]-2-hydroxy-3-t-butylbenzamide, N-[1-(hydroxymethyl)-1-methyl-2-hydroxyethyl]-4-hydroxy-3-t-butylbenzamide, N-[1-(hydroxymethyl)-1-methyl-2-hydroxyethyl]-2-hydroxy-3-t-butyl-5-methylbenzamide, N-[1-(hydroxymethyl)-1-methyl-2-hydroxyethyl]-4-hydroxy-3-t-butyl-5-methylbenzamide, N-[1-(hydroxymethyl)-1-methyl-2-hydroxyethyl]-2-hydroxy-3,5-di-t-butylbenzamide, N-[1-(hydroxymethyl)-1-methyl-2-hydroxyethyl]-4-hydroxy-3,5-di-t-butylbenzamide, N-[1-(hydroxymethyl)-1-methyl-2-hydroxyethyl]-3-(2-hydroxy-3-t-butylphenyl)propionamide, N-[1-(hydroxymethyl)-1-methyl-2-hydroxyethyl]-3-(4-hydroxy-3-t-butylphenyl)propoionamide, N-[1-(hydroxymethyl)-1-methyl-2-hydroxyethyl]-3-(2-hydroxy-3-t-butyl-5-methylphenyl)propionamide, N-[1-(hydroxymethyl)-1-methyl-2-hydroxyethyl]-3-(4-hydroxy-3-t-butyl-5-methylphenyl)propionamide, N-[1-(hydroxymethyl)-1-methyl-2-hydroxyethyl]-3-(2-hydroxy-3,5-di-t-butylphenyl)propionamide, N-[1-(hydroxymethyl)-1-methyl-2-hydroxyethyl]-3-(4-hydroxy-3,5-di-t-butylphenyl)propionamide, N-methyl-N-[1-(hydroxymethyl)-1-methyl-2-hydroxyethyl]-3-(2-hydroxy-3-t-butylphenyl)propionamide, N-methyl-N-[1-(hydroxymethyl)-1-methyl-2-hydroxyethyl]-3-(4-hydroxy-3-t-butylphenyl)propionamide, N-methyl-N-[1-(hydroxymethyl)-1-methyl-2-hydroxyethyl]-3-(2-hydroxy-3-t-butyl-5-methylphenyl)propionamide, N-methyl-N-[1-(hydroxymethyl)-1-methyl-2-hydroxyethyl]-3-(4-hydroxy- 3-t-butyl-5-methylphenyl)propionamide, N-methyl-N-[1-(hydroxymethyl)-1-methyl-2-hydroxyethyl]-3-(2-hydroxy-3,5-di-t-butylphenyl)propionamide, N-methyl-N-[1-(hydroxymethyl)-1-methyl-2-hydroxyethyl]-3-(4-hydroxy-3,5-di-t-butylphenyl)propionamide, N-ethyl-N-[1-(hydroxymethyl)-1-methyl-2-hydroxyethyl]-3-(2-hydroxy-3-t-butylphenyl)propionamide, N-ethyl-N-[1-(hydroxymethyl)-1-methyl-2-hydroxyethyl]-3-(4-hydroxy-3-t-butylphenyl)propionamide, N-ethyl-N-[1-(hydroxymethyl)-1-methyl-2-hydroxyethyl]-3-(2-hydroxy-3-t-butyl-5-methylphenyl)propionamide, N-ethyl-N-[1-(hydroxymethyl)-1-methyl-2-hydroxyethyl]-3-(4-hydroxy-3-t-butyl-5-methylphenyl)propionamide, N-ethyl-N-[1-(hydroxymethyl)-1-methyl-2-hydroxyethyl]-3-(2-hydroxy-3,5-di-t-butylphenyl)propionamide, N-ethyl-N-[-1-(hydroxymethyl)-1-methyl-2-hydroxyethyl]-3-(4-hydroxy-3,5-di-t-butylphenyl)propionamide, N-t-butyl-N-[1-(hydroxymethyl)-1-methyl-2-hydroxyethyl]-3-(2-hydroxy-3-t-butylphenyl)propionamide, N-t-butyl-N-[1-(hydroxymethyl)-1-methyl-2-hydroxyethyl]-3-(4-hydroxy-3-t-butylphenyl)propionamide, N-t-butyl-N-[-(hydroxymethyl)-1-methyl-2-hydroxyethyl]-3-[2-hydroxy-3-t-butyl-5-methylphenyl)propionamide, N-t-butyl-N-[1-(hydroxymethyl)-1-methyl-2-hydroxyethyl]-3-(4-hydroxy-3-t-butyl-5-methylphenyl)propionamide, N-t-butyl-N-[1-(hydroxymethyl)-1-methyl-2-hydroxyethyl]-3-(2-hydroxy-3,5-di-t-butylphenyl)propionamide, N-t-butyl-N-[1-(hydroxymethyl)-1-methyl-2-hydroxyethyl]-3-( 4-hydroxy-3,5-di-t-butylphenyl)propionamide, N-[1-(hydroxymethyl)-1-ethyl-2-hydroxyethyl]-2-hydroxy-3-t-butylbenzamide, N-[1-(hydroxymethyl)-1-ethyl-2-hydroxyethyl]-4-hydroxy-3-t-butylbenzamide, N-[1-(hydroxymethyl)-1-ethyl-2-hydroxyethyl]-2-hydroxy-3-t-butyl-5-methylbenzamide, N-[1-(hydroxymethyl-)-1-ethyl-2-hydroxyethyl]-4-hydroxy-3-t-butyl-5-methylbenzamide, N-[1-(hydroxymethyl)-1-ethyl-2-hydroxyethyl]-2-hydroxy-3,5-di-t-butylbezamide, N-[1-(hydroxymethyl)-1-ethyl-2- hydroxyethyl]-4-hydroxy-3,5-di-t-butylbenzamide, N-[1-(hydroxymethyl)-1-ethyl-2-hydroxyethyl]-3-(2-hydroxy-3-t-butylphenyl)propionamide, N-[1-(hydroxymethyl)-1-ethyl-2-hydroxyethyl]-3-(4-hydroxy-3-t-butylphenyl) propionamide, N-[1-(hydroxymethyl)-1-ethyl-2-hydroxyethyl]-3-(2-hydroxy-3-t-butyl-5-methylphenyl) propionamide, N-[1-(hydroxymethyl)-1-ethyl-2-hydroxyethyl]-3-(4-hydroxy-3-t-butyl-5-methylphenyl) propionamide, N-[1-(hydroxymethyl)-1-ethyl-2-hydroxyethyl]-3-(2-hydroxy-3,5-di-t-butylphenyl) propionamide, N-[1-(hydroxymethyl)-1-ethyl-2-hydroxyethyl]-3-(4-hydroxy-3,5-di-t-butylphenyl) propionamide, N-methyl-N-[1-(hydroxymethyl)-1-ethyl-2-hydroxyethyl]-3-(2-hydroxy-3-t-butylphenyl) propionamide, N-methyl-N-[1-(hydroxymethyl)-1-ethyl-2-hydroxyethyl]-3-(4-hydroxy-3-t-butylphenyl) propionamide, N-methyl-N-[1-(hydroxymethyl)-1-ethyl-2-hydroxyethyl]-3-(2-hydroxy-3-t-butyl-5-methylphenyl) propionamide, N-methyl-N-[1-(hydroxymethyl)-1-ethyl-2-hydroxyethyl]-3-(4-hydroxy-3-t-butyl-5-methylphenyl) propionamide, N-methyl-N-[1-(hydroxymethyl)-1-ethyl-2-hydroxyethyl]-3-(2-hydroxy-3,5-di-t-butylphenyl) propionamide, N-methyl-N-[1-(hydroxymethyl)-1-ethyl-2-hydroxyethyl]-3-(4-hydroxy-3,5-di-t-butylphenyl) propionamide, N-ethyl-N-[1-(hydroxymethyl)-1-ethyl-2-hydroxyethyl]-3-(2-hydroxy-3-t-butylphenyl) propionamide, N-ethyl-N-[-(hydroxymethyl)-1-ethyl-2-hydroxyethyl]-3-(4-hydroxy-3-t-butylphenyl) propionamide, N-ethyl-N-[1-(hydroxymethyl)-1-ethyl-2-hydroxyethyl]-3-(2-hydroxy-3-t-butyl-5-methylphenyl) propionamide, N-ethyl-N-[1-(hydroxymethyl)-1-ethyl-2-hydroxyethyl]-3-(4-hydroxy-3-t-butyl-5-methylphenyl) propionamide, N-ethyl-N-[1-(hydroxymethyl)-1-ethyl-2-hydroxyethyl]-3-(2-hydroxy-3,5-di-t-butylphenyl) propionamide, N-ethyl-N-[1-(hydroxymethyl)-1-ethyl-2-hydroxyethyl]-3-(4-hydroxy-3,5-di-t-butylphenyl) propionamide, N-t-butyl-N-[1-(hydroxymethyl)-1-ethyl-2-hydroxyethyl]-3-(2-hydroxy-3-t-butylphenyl) propionamide, N-t-butyl-N-[1-(hydroxymethyl)-1-ethyl-2-hydroxyethyl]-3-(4-hydroxy-3-t-butylphenyl) propionamide, N-t-butyl-N-[1-(hydroxymethyl)-1-ethyl-2-hydroxyethyl]-3-(2-hydroxy-3-t-butyl-5-methylphenyl) propionamide, N-t-butyl-N-[1-(hydroxymethyl)-1-ethyl-2-hydroxyethyl]-3-(4-hydroxy-3-t-butyl-5-methylphenyl) propionamide, N-t-butyl-N-[1-(hydroxymethyl)-1-ethyl-2-hydroxyethyl]-3-1(2-hydroxy-3,5-di-t-butylphenyl) propionamide and N-t-butyl-N-[1-(hydroxymethyl)-1-ethyl-2-hydroxyethyl]-3-(4-hydroxy-3,5-di-t-butylphenyl) propionamide.

These compounds can be produced, for example, by reacting the corresponding aminoalcohol with the corresponding carboxylic acid, carboxylate or halide carboxylate according to the known methods described in USSR Patent No. 1203083 and French Patent No. 2577242.

The hydrolysis resistance of the phosphonites (I) of the present invention can be improved by containing amines, acid-bonded metal salts and the like.

Examples of the amines include trialkanolamines such as triethanolamine, tripropanolamine, tri-i-propanolamine and the like; dialkanolamines such as diethanolamine, dipropanolamine, di-i-propanolamine, tetraethanolethylenediamine, tetra-i-propanolethylenediamine and the like; monoalkanolamines such as dibutylethanolamine, dibutyl-i-propanolamine and the like; aromatic amines such as 1,3,5-trimethyl-2,4,6-triazine and the like; alkylamines such as dibutylamine, piperidine, 2,2,6,6,-tetramethylpiperidine, 4-hydroxy-2,2,6,6-tetramethylpiperidine and the like; polyalkylenepolyamines such as hexamethylenetetramine, triethylenediamine, triethylenetetramine, tetraethylenepentamine and the like; and hindered amine photostabilizers described hereinafter.

Furthermore, there can also be used a long-chain aliphatic amine described in JP-A-61-63686, a compound having a steric hindrance amine group described in JP-A-6-329830, a hindered piperidinyl photostabilizer described in JP-A-7-90270 and an organic amine described in JP-A-7-278164.

A proportion of the amines to be used is normally about 0.01 to 25% by weight based on the phosphites (I).

Typical examples of the acid-bonded metal salt include hydrotalcites. Examples of the hydrotalcites include double salt compounds represented by the following formula:

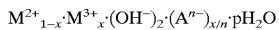

$$M^{2+}_{1-x} \cdot M^{3+}_{x} \cdot (OH^-)_2 \cdot (A^{n-})_{x/n} \cdot pH_2O$$

wherein $M^{2+}$ represents Mg, Ca, Sr, Ba, Zn, Pb, Sn and/or Ni; $M^{3+}$ represents Al, B or Bi; n represents a numerical value of 1 to 4; x represents a numerical value of 0 to 0.5; p represents a numerical value of 0 to 2; and $A^{n-}$ represents an anion having a valency of n.

Specific examples of the amino having a valence of n represented by $A^{n-}$ include $OH^-$, $Cl^-$, $Br^-$, $I^-$, $ClO_4^-$, $HCO_3^-$, $C_6H_5COO^-$, $CO_3^{2-}$, $SO^{2-}$, $-OOCCOO-$, $(CHOHCO)_2^{2-}$, $C_2H_4(COO)_2^{2-}$, $(CH_2COO)_2^{2-}$, $CH_3CHOHCOO-$, $SiO_3^{2-}$, $SiO_4^{4-}$, $Fe(CN)_6^{4-}$, $BO_3^{3-}$, $PO_4^{3-}$, $HPO_4^{2-}$ and the like.

Particularly preferred one among them represented by the above formula include, for example, hydrotalcites represented by the following formula:

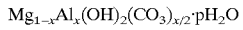

$$Mg_{1-x}Al_x(OH)_2(CO_3)_{x/2} \cdot pH_2O$$

wherein x and p are as defined above.

The hydrotalcites may be natural or synthetic products, and can be used regardless of crystal structure and crystal particle diameter thereof.

Furthermore, an ultrafine zinc oxide described in JP-A-6-329830 and an inorganic compound described in JP-A-7-278164 can also be used.

A proportion of the acid-bonded metal salt to be used is normally about 0.01 to 25% by weight based on the phosphites (I).

The phosphonites (I) of the present invention are effective for stabilizing the organic material against heat deterioration and oxidization deterioration. Examples of the organic material which can be stabilized by phosphonites (I) of the present invention include the followings. They can be stabilized alone or in combination thereof. The organic material which can be stabilized by phosphonites (I) of the present invention are not limited to these organic materials.

(1) polyethylene, for example, high-density polyethylene (HD-PE), low-density polyethylene (LD-PE) and straight-chain low-density polyethylene (LLDPE)
(2) polypropylene
(3) methylpentene polymer
(4) EEA (ethylene/ethyl acrylate copolymer) resin
(5) ethylene/vinyl acetate copolymer resin
(6) polystyrenes, for example, polystyrene, poly(p-methylstyrene) and poly(α-methylstyrene)
(7) As (acrylonitrile/styrene copolymer) resin
(8) ABS (acrylonitrile/butadiene/styrene copolymer) resin
(9) AAS (special acrylic rubber/acrylonitrile/styrene copolymer) resin
(10) ACS (acrylonitrile/chlorinated polyethylene/styrene copolymer) resin
(11) chlorinated polyethylene, polychloroprene, chlorinated rubber

(12) polyvinyl chloride, polyvinylidene chloride
(13) methacrylic resin
(14) etyhylene/vinyl alcohol copolymer resin
(15) fluororesin
(16) polyacetal
(17) grafted polyphenylene ether resin and polyphenylene sulfide resin
(18) polyurethane
(19) polyamide
(20) polyester resin, for example, polyethylene terephthalate and polybutylene terephthalate
(21) polycarbonate
(22) polyacrylate
(23) polysulfone, polyether ether ketone, polyether sulfone
(24) thermoplastic resin such as aromatic polyester resin, etc.
(25) epoxy resin
(26) diallyl phthalate prepolymer
(27) silicone resin
(28) unsaturated polyester resin
(29) acrylic-modified benzoguanamine resin
(30) benzoguanamine/melamine resin
(31) thermosetting resin such as urea resin, etc.
(32) polybutadiene
(33) 1,2-polybutadiene
(34) polyisoprene
(35) styrene/butadiene copolymer
(36) butadiene/acrylonitrile copolymer
(37) ethylene/propylene copolymer
(38) silicone rubber
(39) epichlorohydrin rubber
(40) acrylic rubber
(41) natural rubber
(42) chlorinated rubber paint
(43) polyester resin paint
(44) urethane resin paint
(45) epoxy resin paint
(46) acrylic resin paint
(47) vinyl resin paint
(48) aminoalkyd resin paint
(49) alkyd resin
(50) nitrocellulose resin paint
(51) oil-based paint
(52) wax
(53) lubricating oil Among them, the thermoplastic resin, particularly polyolefin such as polyethylene (e.g. HD-PE, lD-PE, LIDPE, etc.) and polyolefin (e.g. polypropylene, etc.), and the engineering resin such as polyamide, polyethylene terephthalate, polybutylene terephthalate and polycarbonare, are more suitable to be stabilized by phosphonites (I) of the present invention.

The polyolefins are not specifically limited. For example, they may be those obtained by the radical polymerization or those produced by the polymerization using a catalyst containing a metal of Group IVb, Vb, VIb or VIII of the periodic table. The catalyst containing such a metal may be a metal complex which is coordinated by one or more ligands, for example, oxide which is coordinated by a π or σ bond, halogenated compound, alcolate, ester, aryl and the like, and these complexes may be used as it is, or a base material such as magnesium chloride, titanium chloride, alumina, silicon oxide, etc. may carry the complexes.

As the polyolefin, for example, there are preferably used those produced by using Ziegler-Natta catalyst, TNZ catalyst, metallocene catalyst, Phillips catalyst and the like.

Also the engineering resin is not specifically limited. The polyamide resin may be those which have an amide bond at the polymer chain and can be molten with heating. For example, they may be produced by any method such as condensation reaction between diamines and dicarboxylic acids, condensation reaction of aminocarboxylic acids and ring opening polymerization of lactams. Typical examples thereof include nylon 66, nylon 69, nylon 610, nylon 612, poly-bis(p-aminocyclohexyl)methanedodecamide, nylon 46, nylon 6, nylon 12 and copolymers (e.g. nylon 66/6 as a copolymer of nylon 66 and nylon 6, nylon 6/12, etc.).

The polyester resin may be those which have an ester bond at the polymer chain and can be molten with heating, and examples thereof include polyester obtained by the polycondensation between dicarboxylic acids and a dihydroxy compound. The polyester may be a homopolyester or a copolyester.

The polycarbonate may be those which have a carbonate bond at the polymer chain and can be molten with heating, and examples thereof include polycarbonate obtained by reacting an aromatic hydroxy compound and/or a small amount of polyhydroxy compound with a carbonate precursor such as phosgene, diphenyl carbonate, etc. in the presence of a solvent, an acid receptor and a molecular weight adjustor. The polycarbonate resin may be straight-chain or branched resin, or may be a copolymer.

When the organic material is stabilized by containing the phosphonites (I) of the present invention, the phosphonites (I) are normally formulated in an amount of about 0.01 to 5 parts by weight, preferably about 0.03 to 3 parts by weight, more preferably about 0.05 to 1 parts by weight, based on 100 parts by weight of the organic material. When the amount is less than 0.01 parts by weight, the stabilizing effect is not sufficient, necessarily. On the other hand, even when the amount exceeds 5 parts by weight, the improvement of the effect corresponding to the amount is no obtained and it is economically disadvantageous.

When the phosphonites (I) of the present invention are contained in the organic material, if necessary, there can also be contained other additives such as phenol antioxidant, sulfur antioxidant, phosphorous antioxidant, ultraviolet absorber, photostabilizer, peroxide scavenger, polyamide stabilizer, hydroxylamine, lubricant, plasticizer, flame retardant, nucleating agent, metal inactivating agents antistatic agent, pigment, filler, pigment, anti-blocking agent, surfactant, processing aid, foaming agent, emulsifier, brightener, calcium stearate, neutralizing agent (e.g. hydrotalcite, etc.), coloring modifier (e.g. 9,10-dihydro-oxa-10-phosphophenanthrene-10-oxide, etc.) and co-stabilizer (e.g. benzofurans, indolines, etc. described in U.S. Pat. Nos. 4,325,853, 4,338,244, 5,175,312, 5,216,053, 5,252,643 and 4,316,611, DE-A-4,316,622 and 4,316,876, and EP-A-589, 839 and 591,101). These additives can be formulated together with the phosphites (I), and also be formulated in the stage other than the stage where the phosphites (I) are formulated.

Examples of the phenol antioxidant include the followings.

(1) Examples of alkylated monophenol 2,6-di-t-butyl-4-methylphenol, 2,4,6-tri-t-butylphenol, 2,6-di-t-butyl-4-butylphenol, 2-t-butyl-4,6-dimethylphenol, 2,6-di-t-butyl-4-ethrylphenol, 2,6-di-t-butyl-4-n-butylphenol, 2,6-di-t-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-t-butyl-4-methoxymethylphenol, 2,6-di-nonyl-4-methylphenol, 2,4-dimethyl-6-(1'-methylundecyl-1'-yl)phenol, 2,4-dimethyl-6'-(1'-methylheptadecyl-1'-yl)phenol, 2,4-dimethyl-6-(1'-methyltridecyl-1'-yl)phenol and a mixture thereof.

(2) Examples of alkylthiomethylphenol 2,4-dioctylthiomethyl-6-t-butylphenol, 2,4-dioctylthiomethyl-6-methylphenol, 2,4-dioctylthiomethyl-6-ethylphenol, 2,6-didodecylthiomethyl-4-nonylphenol and a mixture thereof (3) Examples of hydroquinone and alkylated hydroquinone 2,6-di-t-butyl-4-methoxyphenol, 2,5-di-t-butylhydroquinone, 2,5-di-t-amylhydroquinone, 2,6-diphenyl-4-octadecyloxyphenol, 2,6-di-t-butylhydroquinone, 2,5-di-t-butyl-4-hydroxyanisole, 3,5-di-t-butyl-4-hydroxyphenyl stearate, bis(3,5-d2-t-butyl-4-hydroxyphenyl)adipate and a mixture thereof (4) Examples of tocopherol α-tocopherol, β-tocopherol, γ-tocopherol, δ-tocopherol and a mixture thereof (5) Examples of hydroxylated thiodiphenyl ether 2,2'-thiobis(6-t-butylphenol), 2,2'-thiobis(4-methyl-6-t-butylphenol), 2,2'-thiobis(4-octylphenol), 4,4'-thiobis(3-methyl-6-t-butylphenol), 4,4'-thiobis(2-methyl-6-t-butylphenol), 4,4'-thiobis(3,6-di-t-amylphenol), 4,4'-(2,6-dimethyl-4-hydroxyphenyl)disulfide and the like (6) Examples of alkylidenebisphenol and derivative thereof 2,2'-methylenebis(4-methyl-6-t-butylphenol), 2,2'-methylenebis(4-ethyl-6-t-butylphenol), 2,2'-methylenebis[4-methyl-6-(α-methylcyclohexyl)phenol)], 2,2'-methylenebis(4-methyl-6-cyclohexylphenol), 2,2'-methylenebis(4-methyl-6-nonylphenol), 2,2'-methylenebis(4,6-di-t-butylphenol)], 2,2'-ethylidenebis(4,6-di-t-butylphenol), 2,2'-ethylidenebis(4-isobutyl-6-t-butylphenol), 2,2'-methylenebis[6-(α-methylbenzyl)-4-nonylphenol], 2,2'-methylenebis[6-(α, α-dimethylbenzyl)-4-nonylphenol), 4,4'-methylenebis(6-t-butyl-2-methylphenol), 4,4'-methylenebis(2,6-di-t-butylphenol), 4,4'-butylidenebis(3-methyl-6-t-butylphenol), 1,1-bis(4-hydroxyphenyl)cyclohexane, 1,1-bis(5-t-butyl-4-hydroxy-2-methylphenyl)butane, 2,6-bis[3-t-butyl-5-methyl-2-hydroxybenzyl)-4-methylphenol, 1,1,3-tris(5-t-butyl-4-hydroxy-2-methylphenyl)butane, 1,1-bis(5-t-butyl-4-hydroxy-2-methylphenyl)-3-n-dodecylmercaptobutane, bis[3,3-bis-3'-t-butyl-4'-hydroxyphanyl)butyrate], bis(3-t-butyl-4-hydroxy-5-methylphenyl)dicyclopentadiene, bis[2-(3'-t-butyl-2'-hydroxy-5'-methylbenzyl)-6-t-butyl-4-methylphenyl]terephthalate, 1,1-bis(3,5-dimethyl-2-hydroxyphenyl)butane, 2,2-bis(3,5-di-t-butyl-4-hydroxyphenyl)propane, 2,2-bis(5-t-butyl-4-hydroxy-2-methylphenyl)-4-n-dodecylmercaptobutane, 1,1,5,5-tetra(5-t-butyl-4-hydroxy-2-methylphenyl)pentane, 2-t-butyl-6-(3'-t-butyl-5'-methyl-2'-hydroxybenzyl)-4-methylphenyl acrylate, 2,4-di-t-pentyl-6-[1-(2-hydroxy-3,5-di-t-pentylphenyl)ethyl]phenyl acrylate and a mixture thereof.

(7) Examples of O-, N- and S-benzyl derivative 3,5,3',5'-tetra-t-butyl-4,4'-dihydroxydibenzyl ether, octadodecyl-4-hydroxy-3,5-dimethylbenzylmercapto acetate, tris(3,5-di-t-butyl-4-hydroxybenzyl)amine, bis(4-t-butyl- 3-hydroxy-2,6-dimethylbenzyl)dithioterephthalate, bis(3,5-di-t-butyl-4-hydroxybenzyl)sulfide, isooctyl-3,5-di-t-butyl-4-hydroxybenzylmercapto acetate and a mixture thereof (8) Examples of hydroxybenzylated malonate derivative dioctadecyl-2,2-bis(3,5-di-t-butyl-2-hydroxybenzyl)malonate, dioctadecyl-2-(3-t-butyl-4-hydroxy-5-methylbenzyl)malonate, didodecylmercaptoethyl-2,2-bis(3,5-di-t-butyl-4-hydroxybenzyl)malonate, bis[4-(1,1,3,3-tetramethylbutyl)phenyl]-2,2-bis(3,5-di-t-butyl-4-hydroxybenzyl)malonate and a mixture thereof (9) Examples of aromatic hydroxybenzyl derivative 1,3,5-trimethyl-2,4,6-tris(3,5-di-t-butyl-4-hydroxybenzyl)benzene, 1,4-bls(3,5-di-t-butyl-4-hydroxybenzyl)-2,3,5,6-tetramethylbenzene, 2,4,6-tris(3,5-t-butyl-4-hydroxybenzyl)phenol and a mixture thereof

(10) Examples of triazine derivative 2,4-bis(n-octylthio)-6-(4-hydroxy-3,5-di-t-butylanilino)-1,3,5-triazine, 2-n-octylthio-4,6-bis(4-hydroxy-3,5-di-t-butylanilino)-1,3,5-triazine, 2-n-octylthio-4,6-bis(4-hydroxy-3,5-di-t-butylphenoxy)-1,3,5-triazine, 2,4,6-tris(3,5-di-t-butyl-4-hydroxy)-1,3,5-triazine, tris(4-t-butyl-3-hydroxy-2,6-dimethylbenzyl isocyanurate, tris(3,5-di-t-butyl-4-hydroxybenzyl)isocyanurate, 2,4,6-tris(3,5-di-t-butyl-4-hydroxyphenylethyl)-1,3,5-triazine, 2,4,6-tris(3,5-di-t-butyl-4-hydroxyphenylpropyl)-1,3,5-triazine, tris( 3,5-dicyclohexyl-4-hydroxybenzyl)isocyanurate, tris[2-(3',5'-di-t-butyl-4'-hydroxycinnamoyloxy)ethyl]isocyanurate and a mixture thereof

(11) Examples of benzyl phosphonate derivative dimethyl-3,5-di-t-butyl-4-hydroxybenzyl phosphonate, diethyl-3,5-di-t-butyl-4-hydroxybenzyl phosphonate, dioctadecyl-3,5-di-t-butyl-4-hydroxybenzyl phosphonate, dioctadecyl-5-t-butyl-4-hydroxy-3-methylbenzyl phosphonate, calcium salt of 3,5-di-t-butyl-4-hydroxybenzyl phosphonic acid monoester and a mixture thereof

(12) Examples of acylaminophenol derivative anilide 4-hydroxylaurate, anilide 4-hydroxystearate, octyl-N-(3,5-di-t-butyl-4-hydroxyphenyl)carbanate and a mixture thereof

(13) Ester of β-(3,5-di-t-butyl-4-hydroxyphenyl) propionic acid and the following monohydric or polyhydric alcohol:

methanol, ethanol, octanol, octadecanol, ethylene glycol, 1,3-propanediol, 1,4-butanediol, 1,6-hexanediol, 1,9-nonanediol, neopentyl glycol, diethylene glycol, thioethylene glycol, spiro glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2,2,2]octane and a mixture thereof

(14) Ester of β-(5-t-butyl-4-hydroxy-3-ethylphenyl) propionic acid and the following monohydric or polyhydric alcohol:

methanol, ethanol, octanol, octadecanol, ethylene glycol, 1,3-propanediol, 1,4-butanediol, 1,6-hexanediol, 1,9-nonanediol, neopentyl glycol, diethylene glycol, thioethylene glycol, spiro glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2,2,2]octane and a mixture thereof

(15) Ester of β-(3,5-dicyclohexyl-4-hydroxyphenyl) propionic acid and the following monohydric or polyhydric alcohol:

methanol, ethanol, octanol, octadecanol, ethylene glycol, 1,3-propanediol, 1,4-butanediol, 1,6-hexanediol, 1,9-nonanediol, neopentyl glycol, diethylene glycol, thioethylene glycol, spiro glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2,2,2]octane and a mixture thereof

(16) Ester of 3,5-t-butyl-4-hydroxyphenylacetic acid and the following monohydric or polyhydric alcohol:

methanol, ethanol, octanol, octadecanol, ethylene glycol, 1,3-propanediol, 1,4-butanediol, 1,6-hexanediol, 1,9-nonanediol, neopentyl glycol, diethylene glycol, thioethylene glycol, spiro glycol, triethylene glycol, pentaerythritol, tris(hydroxyethyl)isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2,2,2]octane and a mixture thereof

(17) Examples of amide of β-(3,5-di-t-butyl-4-hydroxyphenyl)propionic acid

N,N'-bis[3-(3',5'-di-t-butyl-4'-hydroxyphenyl)propionyl] hydrazine, N,N'-bis[3-(3',5'-di-t-butyl-4'-hydroxyphenyl) propionyl]hexamethylenediamine, N,N'-bis[3-(3',5'-di-t-butyl-4'-hydroxyphenyl)propionyl] trimethylenediamine and a mixture thereof Examples of the sulfur antioxidant include the followings:

dilauryl 3,3'-thiodipropionate, tridecyl 3,3'-thiodipropionate, dimyristyl 3,3'-thiodipropionate, distearyl 3,3'-thiodipropionate, lauryl stearyl 3,3'-thiodipropionate, neopentanetetraylkis(3-lauryl thiopropionate) and the like.

Examples of the phosphorous antioxidant include the followings:

triphenyl phosphite, tris(nonylphenyl)phosphite, tris(2,4-di-t-butylphenyl)phosphite, trilauryl phosphite, trioctadecyl phosphite, distearyl pentaerythritol diphosphite, diisodecyl pentaerythritol diphosphite, bis(2,4-di-t-butylphenyl) pentaerythritol diphosphite, bis(2,4-di-t-butyl-6-methylphenyl)pentaerythritol diphosphite, bis(2,4-di-t-butyl-6-methylphenyl)pentaerythritol diphosphite, bis(2,6-di-t-butyl-4-methylphenyl)pentaerythritol diphosphite, bis (2,4,6-tri-t-butylphenyl)pentaerythritol diphosphate, tristearyl sorbitol triphosphite, tetrakis(2,4-di-t-butylphenyl)-4,4'-diphenylene diphosphite, 2,2'-methylenebis(4,6-di-t-butylphenyl)2-ethylhexyl phosphite, 2,2'-ethylidenebis(4,6-di-t-butylphenyl)fluoro phosphite, bis (2,4-di-t-butyl-6-methylphenyl)ethyl phosphite, bis(2,4-di-t-butyl-6-methylphenyl)methyl phosphite, (2,4,6-tri-t-butylphenyl)-5-ethyl-5-butyl-1,3,2-oxaphosphorinane, 2,2', 2"-nitrilo[triethyl-tris(3,3',5,5'-tetra-t-butyl-1,1'-biphenyl-2, 2'-diyl)phosphite and a mixture thereof Examples of the ultraviolet absorber include the followings:

(1) Examples of salicylate derivative phenyl salicylate, 4-t-butylphenyl salicylate, 2,4-di-t-butylphenyl 3',5'-di-t-butyl-4'-hydroxybenzoate, 4-t-octylphenyl salicylate, bis(4-t-butylbenzoyl)resorcinol, benzoylresorcinol, hexadecyl 3',5'-di-t-butyl-4'-hydroxybenzoate, octadecyl 3',5'-di-t-butyl-4'-hydroxybenzoate, 2-methyl-4,6-di-t-butylphenyl 3',5'-di-t-butyl-4'-hydroxybenzoate and a mixture thereof (2) Examples of 2-hydroxybenzophenone derivative 2,4-dihydroxybenzophenone, 2-hydroxy-4-methoxybenzophenone, 2-hydroxy-4-octoxybenzophenone, 2,2'-dihydroxy-4-methoxybenzophenone, bis(5-benzoyl-4-hydroxy-2-methoxyphenyl)methane, 2,2',4,4'-tetrahydroxybenzophenone and a mixture thereof (3) Examples of 2-(2'-hydroxyphenyl)benzotriazole 2-(2-hydroxy-5-methylphenyl)benzotriazole, 2-(3',5'-di-t-butyl-2'-hydroxyphenyl)benzotriazole, 2-(5'-t-butyl-2'-hydroxyphenyl)benzotriazole, 2-(2'-hydroxy-5'-t-octylphenyl)benzotriazole, 2-(3-t-butyl-2-hydroxy-5-methylphenyl)-5-chlorobenzotriazole, 2-(3'-s-butyl-2'-hydroxy-5'-t-butylphenyl)benzotriazole, 2-(2'-hydroxy-4'-octyloxypheny)benzotriazole, 2-(3',5'-di-t-amyl-2'-hydroxyphenyl)benzotriazole, 2-[2'-hydroxy-3',5'-bis(α,α-dimethylbenzyl)phenyl]-2H-benzotriazole, 2-[(3'-t-butyl-2'-hydroxyphenyl)-5'-(2-octyloxycarbonylethyl)phenyl]-5-chlorobenzotriazole, 2-[3'-t-butyl-5'-[2-(2-ethylhexyloxy) carbonylethyl]-2'-hydroxyphenyl]-5-chlorobenzotriazole, 2-[3'-t-butyl-2'-hydroxy-5'-(2-methoxycarbonylethyl) phenyl]-5-chlorobenzotriazole, 2-[3'-t-butyl-2'-hydroxy-5'-(2-methoxycarbonylethyl)phenyl]benzotriazole, 2-[3'-t-butyl-2'-hydroxy-5-(2-octyloxycarbonylethyl)phenyl] benzotriazole, 2-[3'-t-butyl-2'-hydroxy-5'-[2-(2-ethylhexyloxy)carbonylethyl]phenyl]benzotriazole, 2-[2-hydroxy-3-(3,4,5,6-tetrahydrophthalimidemethyl)-5-methylphenyl]benzotriazole, 2-(3',5'-di-t-butyl-2-hydroxyphenyl)-5-chlorobenzotriazole, mixture of 2-(3'-dodecyl-2'-hydroxy-5'-methylphenyl)benzotriazole and 2-[3'-t-butyl-2'-hydroxy-5'-( 2-isooctyloxycarbonylethyl) phenyl]benzotriazole, 2,2'-methylenebis[6-(2H-benzotriazol-2-yl)-4-(1,1,3,3-tetramethylbutyl)phenol, 2,2'-methylenebis[4-t-butyl-6-(2H-benzotriazol-2-yl)phenol], condensate of poly(3-11)(ethylene glycol) and 2-[3'-t-butyl-2'-hydroxy-5'-(2-methoxycarbonylethyl)phenyl] benzotriazole, condensate of poly(3-11)(ethylene glycol) and methyl 3-[3-(2H-benzotriazol-2-yl)-5-t-butyl-4-hydroxyphenyl]propionate, 2-ethylhexyl 3-[3-t-butyl-5-(5-chloro-2H-benzotriazol-2-yl)-4-hydroxyphenyl]propionate, octyl 3-[3-t-butyl-5-(5-chloro-2H-benzotriazol-2-yl)-4-hydroxyphenyl]propionate, methyl 3-[3-t-butyl-5-(5-chloro-2H-benzotriazol-2-yl)-4-hydroxyphenyl]propionate, 3-[3-t-butyl-5-(5-chloro-2H-benzotriazol-2-yl)-4-hydroxyphenyl] propionic acid and a mixture thereof.

Examples of the photostabilizer include the followings.

(1) Examples of hindered amine photostabilizer bis(2,2,6,6-tetramethyl-4-piperidyl)sebacate, bis (2,2,2,66-tetramethyl-4-piperidyl)succinate, bis(1,2,2,6,6-pentamethyl-4-piperidyl)sebacate, bis(N-octoxy-2,2,6,6-tetramethyl-4-piperidyl)sebacate, bis(N-benzyloxy-2,2,6,6-tetramethyl-4-piperidyl)sebacate, bis(N-cyclohexyloxy-2,2, 6,6-tetramethyl-4-piperidyl)sebacate, bis(1,2,2,6,6-pentamethyl-4-piperidyl) 2-(3,5-di-t-butyl-4-hydroxybenzyl)-2-butylmalonate, bis(1-acrolyl-2,2,6,6-tetramethyl-4-piperidyl) 2,2-bis(3,5-di-t-butyl-4-hydroxybenzyl)-2-butylmalonate, bis(1,2,2,6,6-penatmethyl-4-piperidyl decanedioate, 2,2,6,6-tetramethyl-4-piperidyl methacrylate, 4-[3-(3,5-di-t-butyl-4-hydroxyphenyl)propionyloxy]-1-[2-(3-(3,5-di-t-butyl-4-hydroxyphenyl)propionyloxy)ethyl]-2,2,6,6-tetramethylpiperidine, 2-methyl-2-(2,2,6,6-tetramethyl-4-piperidyl)amino-N-(2,2,6,6-tetramethyl-4-piperidyl) propionamide, tetarkis(2,2,6,6-tetramethyl-4-piperidyl) 1,2, 3,4-butaneteracarboxylate, tetrakis (1,2,2,6,6-pentamethyl-4-piperidyl) 1,2,3,4-butanetetracarboxylate, mixed esterified product of 1,2,3,4-butanetetracarboxylic acid and 1,2,2,6,6-pentamethyl-4-piperidinol and 1-tridecanol, mixed esterified product of 1,2,3,4-butanetetracarboxylic acid and 2,2,6,6-tetramethyl-4-piperidinol and 1-tridecanol, mixed esterified product of 1,2,3,4-butanetetracarboxylic acid and 1,2,2,6,6-pentamethyl-4-piperidinol and 3,9-bis(2-hydroxy-1,1-dimethylethyl)-2,4,8,10-tetraoxaspiro[5.5]undecane, mixed esterified product of 1,2,3,4-butanetetracarboxylic acid and 2,2,6,6-tetarmethyl-4-piperidinol and 3,9-bis(2-hydroxy-1, 1-dimethylethyl)-2,4,8,10-tetraoxaspiro[5.5]undecane, polycondensate of dimethyl succinate and 1-(2-hydroxyethyl)-4-hydroxy-2,2,6,6-tetramethylpiperidine, poly[(6-morpholino-1,3,5-triazin-2,4-diyl)((2,2,6,6-tetramethyl-4-piperidyl)imino)hexamethylene ((2,2,6,6-tetramethyl-4-piperidyl)imino)], poly[(6-(1,1,3,3-tetramethylbutyl)imino-1,3,5-triazin-2,4-diyl ((2,2,6,6- tetramethyl-4-piperidyl)imino)hexamethylene (( 2,2,6,6-tetramethyl-4-piperidyl)imino)], polycondensate of N,N'-bis(2,2,6,6-tetramethyl-4-piperidyl)hexamethylenediamine and 1,2-bromoethane, N,N',4,7-tetrakis[4,6-bis(N-butyl-N-(2,2,6,6-tetramethyl-4-piperidyl)amino)-1,3,5-triazin-2-yl]-4,7-diazadecane-1,10 diamine, N,N',4-tris[4,6-bis(N-butyl-N-(2,2,6,6-tetramethyl-4-piperidyl)amino)-1,3,5-triazin-2-yl]-4,7-diazadecane-1,10 diamine, N,N',4,7-tetrakis[4,6-bis(N-butyl-N-(1,2,2,6,6-pentamethyl-4-piperidyl)amino)-1,3,5-triazin-2-yl]-4,7-diazadecane-1,10 diamine, N,N',4-tris[4,6-bis(N-butyl-N-(1,2,2,6,6-pentamethyl-4-piperidyl)amino)-1,3,5-triazin-2-yl]-4,7-diazadecane-1,10 diamine and a mixture thereof (2) Examples of acrylate photostabilizer ethyl α-cyano-β,β-diphenylacrylate, isooctyl α-cyano-β,β-diphenylacrylate, methyl α-carbomethoxycinnamate, methyl α-cyano-β-methyl-methoxycinnamate, butyl α-cyano-β-methyl-p-methoxycinnamate, methyl α-carbomethoxy-p-methoxycinnamate and N-(β-carbomethoxy-β-cyano-vinyl)-2-methylindoline and a mixture thereof (3) Examples of nickel photostabilizer nickel complex of 2,2'-thiobis-[4-(1,1,3,3-tetramethylbutyl)phenol], nickel dibutyldithiocarbamate, nickel salt of monoalkyl ester, nickel complex of ketoxime and a mixture thereof (4) Examples of oxamide photostabilizer 4,4'-dioctyloxyoxanilide, 2,2-diethoxyoxanilide, 2,2'-dioctyloxy-5,5'-di-t-butylanilide, 2,2'-didodecyloxy-5,5'-di-t-butylanilide, 2-ethoxy-2'-ethyloxanilide, N,N'-bis(3-dimethylaminopropyl)oxamide, 2-ethoxy-5-t-butyl-2'-ethoxyanilide, 2-ethoxy-5,4'-di-t-butyl-2'-ethyloxanilide and a mixture thereof (5) Examples of 2-(2-hydroxyphenyl)-1,3,5-triazine photostabilizer 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(4-methylphenyl)-1,3,5-triazine, 2-[2-hydroxy-4-(2-hydroxy-3-butyloxypropoxy)phenyl]-4,6-bis(2,4-dimethylphenyl)-1,3,5-triazine, 2-[2-hydroxy-4-(2-hydroxy-3-octyloxyphenyl)-4,6-bis(2,4-dimethylphenyl)-1,3,5-triazine and a mixture thereof.

Examples of the metal inactivating agent include the followings:

N,N'-diphenyloxamide, N-salicylal-N'-salicyloylhydrazine, N,N'-bis(salicyloyl)hydrazine, N,N'-bis(3,5-di-t-butyl-4-hydroxyphenylpropionyl)hydrazine, 3-salicyloylamino-1,2,4-triazole, bis(benzylidene)oxalyl dihydrazide, oxalinide, isophthaloyl dihydrazide, sebacoyl-bisphenyl hydrazide, N,N'-bis(salicyloyl)thiopropionyl dihydrazide and a mixture thereof.

Examples of the peroxide scavenger include ester of β-thiodipropionic acid, mercaptobenzoimidazole, zinc salt of 2-mercaptobenzoimidazole, zinc salt of dibutyldithiocarbamic acid, dioctadecyl disulfide, pentaerythritol tetrakis(β-dodecylmercapto)propionate and a mixture thereof.

Examples of the polyamide stabilizer include copper or divalent manganese salt of iodide or phosphorous compound and a mixture thereof.

Examples of the hydroxyamine include N,N-dibenzylhydroxyamine, N,N-diethylhydroxyamine, N,N-dioctylhydroxyamine, N,N-dilaurylhydroxyamine, N,N-ditetradecylhydroxyamine, N,N-dihexadecylhydroxyamine, N,N-dioctadecylhydroxyamine, N,N-dibenzylhydroxyamine, N,N-dibenzylhydroxyamine, N-hexadecyl-N-octadecylhydroxyamine, N-heptadecyl-N-octadecylhydroxyamine and a mixture thereof.

Examples of the neutralizing agent include calcium stearate, zinc stearate, magnesium stearate, hydrotalcite (basic magnesium aluminum hydroxycarbonate hydride), melamine, amine, polyamide, polyurethane and a mixture thereof.

Examples of the lubricant include aliphatic hydrocarbon (e.g. paraffin, wax, etc.), higher aliphatic acid having 8 to 22 carbon atoms, higher aliphatic acid (having 8 to 22 carbon atoms) metal (Al, Ca, Mg, Zn) salt, aliphatic alcohol having 8 to 22 carbon atoms, polyglycol, ester of higher fatty acid having 4 to 22 carbon atoms and aliphatic monohydric alcohol having 4 to 18 carbon atoms, higher aliphatic amide having 8 to 22 carbon atoms, silicone oil, rosin derivative and the like.

Examples of the nucleating agent include the followings:
sodium 2,2'-methylenebis(4,6-di-t-butylphenyl) phosphate, [phosphoric acid-2,2'-methylenebis(4,6-di-t-butylphenyl)]dihydroxyaluminum, bis[phosphoric acid-2,2'-methylenebis(4,6-di-t-butylphenyl)] dihydroxyaluminum, tris[phosphoric acid-2,2'-methylenebis(4,6-di-t-butylphenyl)] aluminum, sodium bis(4,6-di-t-butylphenyl) phosphate, benzoic acid metal salt such as sodium benzoate, aluminum p-t-butylbenzoate, 1,3:2,4-bis(O-benzylidene) sorbitol, 1,3:2,4-bis(O-ethylbenzylidene)sorbitol, 1,3:2,4-bis(O-methylbenzylidene)sorbitol, 1,3-O-3,4-dimethylbenzylidene-2,4-O-benzylidenesorbitol, 1,3-O-benzylidene-2,4-O-3,4-dimethylbenzylidene sorbitol, 1,3:2,4-bis(O-3,4-dimethylbenzylidene)sorbitol, 1,3-O-p-chlorobenzylidene-2,4-O-3,4-dimethylbenzylidene sorbitol, 1,3-O-3,4-dimethylbenzylidene-2,4-O-p-chlorobenzylidene sorbitol, 1,3:2,4-bis(O-p-chlorobenzylidene)sorbitol and a mixture thereof.

Examples of the filler include calcium carbonate, silicate, glass fiber, asbestos, talc, kaoline, mica, barium sulfate, carbon black, carbon fiber, zeolite and a mixture thereof.

Among these additives above, fillers, phenol antioxidant, phosphorous antioxidant, ultraviolet absorber, hindered amine photostabilizer, peroxide scavenger and neutralizing agent are preferably used.

Examples of the particularly preferred phenol antioxidant include the following compounds, and they may be used in combination of the two or more:

2,6-di-t-butyl-4-methylphenol, 2,4,6-tri-t-butylphenol, 2,4-dioctylthiomethyl-6-methylphenol, 2,2'-thiobis(6-t-butylphenol), 4,4'-thiobis(3-methyl-6-t-butylphenol), 2,2'-methylenebis(4-methyl-6-t-butylphenol), 2,2'-methylenebis[4-ethyl-6-t-butylphenol], 2,2'-methylenebis(4-ethyl-6-(α-methylcyclohexyl)phenol], 2,2'-methylenebis(4-methyl-6-cyclohexylphenol), 2,2'-methylenebis(4,6-di-t-butylphenol), 2,2'-ethylidenebis(4,6-di-t-butylphenol), 4,4'-methylenebis(6-t-butyl-2-methylphenol),4,4'-methylenebis(2,6-di-t-butylphenol), 4,4'-mbutylidenebis(3-methyl-6-t-butylphenol), 1,1'-bis(4-hydroxyphenyl)cyclohexane, 1,1-bis(5-t-butyl-4-hydroxy-2-methylphenyl)butane, 1,1,3-tris(5-t-butyl-4-hydroxy-2-methylphenyl)butane, ethylene glycol, bis[3,3-bis-3'-t-butyl-4'-hydroxyphenyl)butyrate], 2-t-butyl-6-(3'-t-butyl-5-methyl-2'-hydroxybenzyl)-4-methylphenyl acrylate, 2,4-di-t-pentyl-6-[1-(2-hydroxy-3,5-di-t-pentylphenyl)ethyl]phenyl acrylate, 2,4,6-tris(3,5-di-t-butyl-4-phneoxy)-1,3,5-triazine, tris(4-t-butyl-3-hydroxy-2,6-dimethylbenzyl)isocyanurate, tris(3,5-di-t-butyl-4-hydroxybenzyl)isocyanurate, tris[2-(3',5'-di-t-butyl-4'- hydroxycinnamoyloxy)ethyl)isocyanurate, diethyl-3,5-di-t-butyl-4-hydroxybenzyl phosphonate, di-n-octadecyl-3,5-di-t-butyl-4-hydroxybenzyl phosphonate, calcium salt of 3,5-di-t-butyl-4-hydroxybenzylphosphonic acid monoester, n-octadecyl 3-(3,5-di-t-butyl-4-hydroxyphenyl)propionate, neopentanetetrayltetrakis(3,5-di-t-butyl-4-hydroxycinnamate), thiodiethylenebis(3,5-di-t-butyl-4-hydroxycinnamate), 1,3,5-trimethyl-2,4,6-tris(3,5-di-t-butyl-4-hydroxybenzyl)benzene, 3,6-dioxaoctamethylenebis(3,5-di-t-butyl-4-hydroxycinnamate), hexamethylenebis(3,5-di-t-butyl-4-hydroxycinnamate), triethylene glycol bis(5-t-butyl]-4-hydroxy-3-methylcinnamate),3,9-bis[2-(3-(3-t-butyl-4-hydroxy-5-methylphenyl)propionyloxy)-1,1-dimethylethyl]-2,4,8,10-tetraoxaspiro [5.5]undecane, N,N'-bis[3-(3',5'-d-t-butyl-4'-hydroxyphenyl)propionyl]hydrazine, N,N'-bis[3-(3',5'-di-t-butyl-4'-hydroxyphenyl)propionyl]hexamethylenediamine and the like.

Examples of the particularly preferred phosphorous antioxidant include the followings, and they may be used in combination of the two or more:

tris(nonylphenyl)phosphite, tris(2,4-di-t-butylphenyl) phosphite, distearyl pentaerythritol diphosphite, bis(2,4-di-t-butylphenyl)pentaerythritol diphosphite, bis(2,4-di-t-butyl-6-methylphenyl)pentaerythritol diphosphite, bis( 2,6-di-t-butyl-4-methylphenyl)pentaerythritol diphosphite, tetrakis(2,4-di-t-butylphenyl)-4,4'-diphenylenediphosphite, 2,2'-methylenebis(4,6-di-t-butylphenyl) 2-ethylhexyl phosphite, 2,2'-ethylidenebis(4,6-di-t-butylphenyl) fluorophosphite, bis(2,4-di-t-butyl-6-methylphenyl) ethylphosphite, 2-(2,4,6-tri-t-butylphenyl)-5-ethyl-5-butyl-1,3,2-oxaphospholinane, 2,2',2"-nitrilo[triethyl-tris(3,3',5,5'-tetra-t-butyl-1,1'-biphenyl-2,2'-diyl)phosphite and the like Examples of the particularly preferred ultraviolet absorber include the followings, and two or more kinds of them can be used.

phenyl salicylate, 4-t-butylphenyl salicylate, 2,4-di-t-butylphenyl 3',5'-di-t-butyl-4'-hydroxybenzoate, 4-t-octylphenyl salicylate, 2,4-dihydroxybenzophenone, 2-hydroxy-4-methoxybenzophenone, 2-hydroxy-4-octoxybenzophenone, 2,2'-dihydroxy-4-methoxybenzophenone, biss(5-benzoyl-4-hydroxy-2-methoxyphenyl)methane, 2,2',4,4'-tetrahydroxybenzophenone, 2-(2-hydroxy-5-methylphenyl) benzotriazole, 2-(3',5'-di-t-butyl-2'-hydroxyphenyl)benzotriazole, 2-(5'-t-butyl-2'-hydroxyphenyl) benzotriazole, 2-(2-hydroxy-5'-t-octylphenyl)benzotriazole, 2-(3-t-butyl-2-hydroxy-5-methylphenyl)-5-chlorobenzotriazole, 2-(3'-s-butyl-2'-hydroxy-5'-t-butylphenyl)benzotriazole, 2-(2'-hydroxy-4'-octyloxyphenyl)benzotriazole, 2-(3',5'-di-t-amyl-2'-hydroxyphenyl)benzotriazole, 2-[2'-hydroxy- 3',5'-bis(α,α-dimethylbenzyl)phenyl]-2H-benzotriazole and the like Examples of the particularly preferred photostabilizer include the followings, and two or more kinds of them can be used.

bis(2,2,6,6-tetramethyl-4-piperidyl)sebacate, bis(1,2,2,6,6-pentamethyl-4-piperidyl)sebacate, bis(N-octoxy-2,2,6,6-pentamethyl-4-piperidyl)sebacate, bis(N-octoxy-2,2,6,6-pentamethyl-4-piperidyl)sebacate, bis(N-benzyloxy-2,2,6,6-tetarmethyl-4-piperidyl)sebacate, bis(N-cyclohexyloxy-2,2,6,6-tetramethyl-4-piperidyl)sebacate, bis(1,2,2,6,6-pentamethyl-4-piperidyl) 2-(3,5-di-t-butyl-4-hydroxybenzyl)-2-butylmalonate, bis(1-acryloyl-2,2,6,6-tetramethyl-4-piperidyl) 2,2-bis(3,5-di-t-butyl-4-hydroxybenzyl)-2-butylmalonate, bis(2,2,6,6-tetramethyl-4-piperidyl)succinate, 2,2,6,6-tetramethyl-4-piperidyl methacrylate, 4-[3-(3,5-di-t-butyl-4-hydroxyphenyl-propionyloxy)-1-[2-(3-(3,5-di-t-butyl-4-hydroxyphenyl) propionyloxy)ethyl]-2,2,6,6-tetramethylpiperidine, 2-methyl-2-(2,2,6,6-tetramethyl-4-piperidyl)amino-N-(2,2,6,6-tetarmethyl-4-piperidyl)propionamide, tetrakis(2,2,6,6-tetramethyl-4-piperidyl) 1,2,3,4-butanetetracarboxylate. tetrakis(1,2,6,6-pentamethyl-4-piperidyl) 1,2,3,4-butanetetracarboxylate, mixed esterified product of 1,2,3,4-butanetetracarboxylic acid and 1,2,2,6,6-pentamethyl-4-piperidinol and 1-tridecanol, mixed esterified product of 1,2,3,4-butanetetracarboxylic acid and 2,2,6,6-tetramethyl-4-piperidinol and 1-tridecanol, mixed esterified product of 1,2,3,4-tetracarboxylic acid and 1,2,2,6,6-pentamethyl-4-piperidinol and 3,9-bis(2-hydroxy-1,1-dimethylethyl)-2,4,8,10-tetraoxaspiro[5.5]undecane, mixed esterified product of 1,2,3,4-butanetetracarboxylic acid and 2,2,6,6-tetarmethyl-4-piperidinol and 3,9-bis(2-hydroxy-1,1-dimethylethyl)-2,4,8,10-tetraoxaspiro[5.5]undecane, polycondensate of dimethyl succinate and 1-(2-hydroxyethyl)-4-hydroxy-2,2,6,6-tetramethylpiperidine, poly[(6-morpholino-1,3,5-triazin-2.4-diyl)((2,2,6,6-tetramethyl-4-piperidyl)imino) hexamethylene ((2,2,6,6-tetramethyl-4-piperidyl)imino)], poly[(6-(1,1,3,3-tetramethylbutyl)imino-1,3,5-triazin-2,4-diyl ((2,2,6,6-tetramethyl-4-piperidyl)imino)hexamethylene ((2,2,6,6-tetramethyl-4-piperidyl)imino)] and the like When the phosphonites (I) and optionally used other additives are formulated in the organic material, known all methods and devices for obtaining a homogeneous mixture can be used. For example, when the organic material is a solid polymer, the phosphites (I) and other additives can be directly dry-blended in the solid polymer, and the phosphite compound or other additives can also formulated in the solid polymer in the form of a masterbatch. When the organic material is a liquid polymer, the phosphonites (I) and other additives can be formulated in the polymer solution during or immediately after polymerization in the form of a solution or a dispersion. On the other hand, when the organic material is a liquid such as oil, the phosphonites (I) and other additives can also be dissolved by direct addition, and the phosphonites (I) and other additives can also be added in the form of being dissolved or dispersed in the liquid medium.

The phosphonites (I) of the present invention have excellent performance as a stabilizer for various organic materials such as thermoplastic resin (e.g. polyolefin, etc.), and the organic material containing this compound is stable to heat and oxidization on production, processing and use, which results in high-quality product.

The following Examples further illustrate the present invention in detail but are not to be construed to limit the scope thereof.

EXAMPLE 1

Production of 3-(3,5-di-t-butyl-4-hydroxyphenyl) propionic acid-3-[(6H-dibenzo[c,e][1,2] oxaphosphorine-6-yl)oxy]ethyl (compound 1)

In a flask equipped with a thermometer, a stirrer and a condenser, 9.4 g of 3-(3,5-di-t-butyl-4-hydroxyphenyl) propionyloxyethanol, 100 ml of toluene and 4.2 g of triethylamine were charged under a nitrogen gas flow. Thereto, 12.9 g of 6-chloro-[(6H-dibenzo[c,e][1,2]oxaphosphorine and 50 ml of toluene was added, and the mixture was maintained at 80° C. for 12 hours.

After cooling to room temperature, the formed hydrochloride of triethylamine was filtered. The filtrate was concentrated and the residue was treated by silica gel chromatography to obtain 1.35 g of a colorless vicous liquid.

Mass spectrometric analysis (FD-MS): m/z 520 Melting point: 151° C. $^1$H-NMR (CDCl$_3$)

1.45 (s, 18H), 2.65 (d, 2H), 2.95 (d, 2H), 3.78 (d, 2H), 4.24 (d, 2H), 5.08 (s, 1H), 7–7.4 (m, 10H) $^{31}$P-NMR (CDCl$_3$) 128 ppm

EXAMPLE 2

Thermal Stability Test of Polypropylene

[Formulation]

Polypropylene (block) 100 Parts by weight

Calcium stearate 0.05 Parts by weight

Compound to be tested 0.05 Parts by weight

C-1: Compound 1 (produced in Example 1)

P-1: 2,10-dimethyl-4,8-di-t-butyl-6-{2-[3-(3-t-butyl-4-hydroxy-5-methylphenyl)propionyloxy]ethoxy}-12H-dibenzo[d,g][1,3,2]dioxaphosphosin P-2: 2,4-di-t-butyl-6-[3,5-di-t-butyl-6-((6H-dibenzo[c,e][1,2]oxaphosphorine-6-yl)oxy)benzyl]phenol Using a 30 mm φ single-screw extruder, the above formulation was repelletized at 250° C. MFR (g/minute) of the resulting pellets was measured at 250° C. under a load of 2160 g for a detention time of 5 minutes by using a melt indexer. The results are shown in Table 1. The smaller the MFR becomes, the better the processing stability.

TABLE 1

|  | Example | Comparative Example | | |
|---|---|---|---|---|
|  | 1 | 1 | 2 | 3 |
| Compound to be tested | C-1 | — | P-1 | P-2 |
| Processing stability | 19.1 | 29.4 | 22.0 | 20.7 |

EXAMPLE 3

Thermal Stability Test of Linear Low-density Polyethylene

[Formulation]

| Unstabilized linear low-density polyethylene | 100 Parts by weight |
|---|---|
| Hydrotalcite | 0.1 Parts by weight |
| Compound to be tested | 0.05 Parts by weight |

C-1: Compound 1 (produced in Example 1)

P-1: 2,10-dimethyl-4,8-di-t-butyl-6-{2-[3-(3-t-butyl-4-hydroxy-5-methylphenyl)propionyloxy]ethoxy}-12H-dibenzo[d,g][1,3,2]dioxaphosphosin P-2: 2,4-di-t-butyl-6-[3,5-di-t-butyl-6-((6H-dibenzo[c,e][1,2]oxaphosphorine-6-yl)oxy)benzyl]phenol Using a 30 mm φ single-screw extruder, the above formulation was repelletized at 250° C. MFR (g/minute) of the resulting pellets was measured at 250° C. under a load of 5000 g for a detention time of 5 minutes by using a melt indexer. The results are shown in Table 2. The smaller the MFR becomes, the better the processing stability.

TABLE 2

|  | Example | Comparative Example | | |
|---|---|---|---|---|
|  | 1 | 1 | 2 | 3 |
| Compound to be tested | C-1 | — | P-1 | P-2 |
| Processing stability | 12.6 | 8.6 | 12.3 | 11.8 |

EXAMPLE 4

Thermal Coloration Test of Linear Low-density Polyethylene

[Formulation]

| Unstabilized linear low-density polyethylene | 100 Parts by weight |
|---|---|
| Hydrotalcite | 0.1 Parts by weight |
| Compound to be tested | 0.05 Parts by weight |

C-1: Compound 1 (produced in Example 1)

P-1: 2,10-dimethyl-4,8-di-t-butyl-6-{2-[3-(3-t-butyl-4-hydroxy-5-methylphenyl)propionyloxy]ethoxy}-12H-dibenzo[d,g][1,3,2]dioxaphosphosin P-2: 2,4-di-t-butyl-6-[3,5-di-t-butyl-6-((6H-dibenzo[c,e][1,2]oxaphosphorine-6-yl)oxy)benzyl]phenol After dry-blending the above formulation, it was kneaded at 230° C. at 10 rpm for 5 minutes by using a laboplast mill, and then pressed at 250° C. to form a sheet having a thickness of 2 mm. A YI value of the sheet was measured. The results are shown in Table 3.

Evaluation criteria are as follows.

○: YI=0 to 5

Δ: YI=5 to 10

X: YI>10

TABLE 1

|  | Example | Comparative Example | |
|---|---|---|---|
|  | 1 | 1 | 2 |
| Compound to be tested | C-1 | P-1 | P-2 |
| Hue | ○ | Δ | X |

What is claimed is:

1. A phosphonite represented by the formula (I):

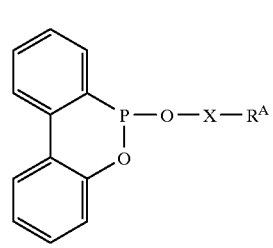

(I)

wherein R$^A$ represents a phenyl group which may be optionally substituted and X is a group represented by the following formula (IV), (V), (VI), (VII), or (VIII):

*—C(O)—A— (IV)

*—B—O—C(O)—A— (V)

*—D—C(O)—O—A— (VI)

*—G—N(R$^1$)—A— (VII)

*—G—N(R$^1$)—C(O)—A— (VIII)

wherein * indicates the bond connecting to the oxygen atom, D represents an alkylene group having 1–8 carbon atoms, A represents a direct bond or an alkylene group having 1–8 carbon atoms, B represents a dihydric alcohol residue, G represents an alkylene group having 2–8 carbon atoms, and R$^1$ represents a hydrogen atom, an alkyl group having 1–8 carbon atoms or a group represented by the following formula (IX):

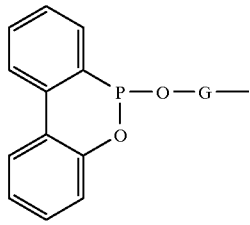

(IX)

wherein G is as defined above.

2. A phosphonite according to claim 1 wherein R$^A$ is a phenyl group substituted with at least one group selected from an alkyl group having 1 to 8 carbon atoms, a cycloalkyl group having 5 to 8 carbon atoms, an alkylcycloalkyl group having 6 to 12 carbon atoms, a aralkyl group having 7 to 12 carbon atoms, a phenyl group, an hydroxyl group, an alkoxy group having 7 to 12 carbon atoms and an aralkyloxy group having 7 to 12 carbon atoms.

3. A phosphonite according to claim 1 wherein R$^A$ is a a phenyl group represented by the formula (X):

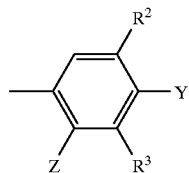

(X)

wherein R$^2$ and R$^3$ independently represent hydrogen, an alkyl group having 1 to 8 carbon atoms, a cycloalkyl group having 5 to 8 carbon atoms, an alkylcycloalkyl group having 6 to 12 carbon atoms, an aralkyl group having 7 to 12 carbon atoms; or a phenyl group and Y and Z independently represent hydrogen, an alkyl group having 1 to 8 carbon atoms, a cycloalkyl group having 5 to 8 carbon atoms, an alkylcycloalkyl group having 6 to 12 carbon atoms, an aralkyl group having 7 to 12 carbon atoms, a phenyl group, a hydroxyl group, an alkoxy group having 1 to 8 carbon atoms or an aralkyloxy group having 7 to 12 carbon atoms.

4. A stabilizer for an organic material, comprising a phosphonite of claim 1 as an active ingredient.

5. A method for stabilizing an organic material, which comprises including the phosphonite of claim 1 in the organic material.

6. The stabilizing method according to claim 5, wherein the organic material is a thermoplastic resin.

7. The stabilizing method according to claim 6, wherein the thermoplastic resin is a polyolefin.

8. A stabilized organic material composition, comprising an organic material, and the phosphonite of claim 1.

9. The composition according to claim 8, wherein the organic material is a thermoplastic resin.

10. The composition according to claim 9, wherein the thermoplastic resin is a polyolefin.

* * * * *